US006333439B1

(12) United States Patent
Shimada

(10) Patent No.: US 6,333,439 B1
(45) Date of Patent: Dec. 25, 2001

(54) BISAZO COMPOUND AND ELECTROPHOTOGRAPHIC PHOTOCONDUCTOR USING THE SAME

(75) Inventor: Tomoyuki Shimada, Shizuoka (JP)

(73) Assignee: Ricoh Company, Ltd., Tokyo (JP)

( * ) Notice: Subject to any disclaimer, the term of this patent is extended or adjusted under 35 U.S.C. 154(b) by 0 days.

(21) Appl. No.: 09/609,901

(22) Filed: Jul. 3, 2000

Related U.S. Application Data

(62) Division of application No. 09/287,662, filed on Apr. 7, 1999.

(30) Foreign Application Priority Data

Apr. 8, 1998 (JP) ........ 10-095969
May 21, 1998 (JP) ........ 10-139974
Sep. 8, 1998 (JP) ........ 10-253905
Feb. 9, 1999 (JP) ........ 11-030873

(51) Int. Cl.[7] ........ C07C 205/06
(52) U.S. Cl. ........ 568/931
(58) Field of Search ........ 568/931

(56) References Cited

U.S. PATENT DOCUMENTS

| | | | |
|---|---|---|---|
| 4,830,943 | 5/1989 | Sasaki et al. | 430/58 |
| 5,344,735 | 9/1994 | Sasaki et al. | 430/83 |
| 5,623,062 | 4/1997 | Sasaki et al. | 534/653 |
| 5,981,124 | 11/1999 | Sasaki et al. | 430/56 |
| 6,103,435 | 8/2000 | Sasaki et al. | 430/56 |

*Primary Examiner*—Fiona T. Powers
(74) *Attorney, Agent, or Firm*—Oblon, Spivak, McClelland, Maier & Neustadt, P.C.

(57) ABSTRACT

An electrophotographic photoconductor has an electroconductive support, and a photoconductive layer formed thereon which contains at least one bisazo compound of formula (I):

(I)

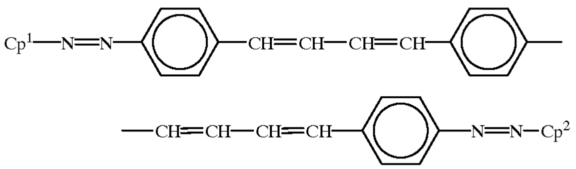

wherein $Cp^1$ and $Cp^2$ are each a coupler radical which may be the same or different. Further, these are disclosed a bisazo compound of formula (II), and raw materials thereof, that is, 1,4-bis[4-(4-nitrophenyl)-1,3-butadienyl]benzene of formula (V), 1,4-bis[4-(4-aminophenyl)-1,3-butadienyl] benzene of formula (VI) and a bis(diazonium salt) compound of formula (III).

3 Claims, 8 Drawing Sheets

BISAZO COMPOUND AND ELECTROPHOTOGRAPHIC PHOTOCONDUCTOR USING THE SAME

This application is a division of application Ser. No. 09/287,662 Filed on Apr. 7,1999, pending.

BACKGROUND OF THE INVENTION

1. Field of the Invention

The present invention relates to an electrophotographic photoconductor comprising a photoconductive layer which contains a bisazo compound. The present invention also relates to above-mentioned bisazo compound which is useful as an organic photoconductive material in the photoconductor and a method of preparing the bisazo compound, and in addition, relates to raw materials for the above-mentioned bisazo compound and the respective preparation methods of those raw materials.

2. Discussion of Background

Conventionally, the photoconductive material for use in the electrophotographic process is roughly divided into two groups, that is, an inorganic photoconductive material and an organic photoconductive material. The above-mentioned electrophotographic process is one of the image forming processes, through which the surface of the photoconductor is charged uniformly in the dark to a predetermined polarity, for instance, by corona charge. The uniformly charged photoconductor is exposed to a light image to selectively dissipate the electric charge of the exposed area, so that a latent electrostatic image is formed on the photoconductor. The thus formed latent electrostatic image is developed into a visible image by use of a toner comprising a coloring agent such as a dye or pigment, and a polymeric material. Such an electrophotographic process is called "Carlson process".

The photoconductor employing the organic photoconductive material is advantageous over that employing the inorganic photoconductive material in terms of the degree of freedom in the wave range of the light to be employed, and the film-forming properties, flexibility, transparency, productivity, toxicity, and manufacturing cost of the photoconductor. In light of the above-mentioned advantages, most of the current photoconductors employ the organic photoconductive material.

Such a photoconductor is repeatedly operated in the copying apparatus employing the above-mentioned electrophotographic process or the like, so that the photoconductor is required to have excellent electrostatic properties, with respect to the photosensitivity, acceptance potential, retentivity of charge, potential stability, residual potential, and spectral sensitivity.

In recent years, the development of data processing apparatus employing the above-mentioned electrophotographic photoconductor is remarkable. In particular, there is a remarkable improvement in the printing quality and the reliability of the digital printer which is capable of converting data into digital signals and recording the data using a light. Such a digital recording system is applied not only to the printer, but also to the copying machine. Thus, the digital copying machine is actively developed. It is supposed that the demand for the digital copying machine will further increase in line with the addition of various data processing functions.

The photoconductor designed for the above-mentioned digital recording system is required to have special characteristics different from those required for the conventional analogue recording system. For instance, a semiconductor laser beam (LD) or a light emitting diode (LED) is widely employed as a light source for the digital recording system because of its compactness, cheapness and high reliability. The wave range of the currently used LD is within the near infrared region, and the wavelength of the currently used LED is 650 nm or more. Therefore, the electrophotographic photoconductors for use with the above-mentioned digital recording system are required to show sufficient sensitivity in the wavelength range from the visible region to the near infrared region.

A specific azo compound is conventionally known as a useful organic photoconductive material, in particular, a charge generation material, in the layered photoconductor. In the above-mentioned layered photoconductor, a charge generation layer and a charge transport layer are successively overlaid on an electroconductive support. The charge generation layer comprises a charge generation material capable of generating a charge carrier when exposed to light, and the charge transport layer comprises a charge transport material serving to efficiently inject the charge carrier generated in the charge generation layer into the charge transport layer and transport the charge carrier.

A variety of azo compounds for use in the photoconductor are conventionally proposed, for example, benzidine bisazo compounds in Japanese Laid-Open Patent Applications 47-37543 and 52-55643, stilbene bisazo compounds in Japanese Laid-Open Patent Application 52-8832, diphenyl hexatriene bisazo compounds in Japanese Laid-Open Patent Application 58-222152, and diphenyl butadiene bisazo compounds in Japanese Laid-Open Patent Application 58-222153.

However, the sensitivity of the electrophotographic photoconductor is slightly decreased when the above-mentioned conventional azo compounds are employed. Therefore, such a photoconductor is not suitable for the high-speed copying machine. Further, the sensitivity of the photoconductor is extremely low in the wavelength range of the LD, so that the photoconductor employing the conventional azo compound cannot be put to practical use in the field of digital recording system. There is an increasing demand for the preparation of an azo compound for use in the electrophotographic photoconductor, that is useful as an organic photoconductive material free of the above-mentioned conventional shortcomings.

There is reported 1,4-bis[4-(3-nitrophenyl)- 1,3-butadienyl]benzene in J. Org. Chem. vol. 24, 1969 (1959) by R. N. McDonald and T. W. Campbell. A bisazo compound can be prepared from the above-mentioned 1,4-bis[4-(3-nitrophenyl)-1,3-butadienyl]benzene. However, the bisazo compound thus obtained does not show any absorption in the wavelength range of the semiconductor laser. This is because each azo group is bonded to phenyl group at the m-position in the large-size conjugated system of 1,4-bis[4-phenyl-1,3-butadienyl]benzene, so that m-phenylene bonds insulate the conjugation in the molecule. This mechanism is detailed in Nippon Kagaku Kaishi 1986, (3), P.379–386. Therefore, such a bisazo compound is not useful as the organic photoconductive material for use in the photoconductor that is required to show high sensitivity with respect to the wavelength of the currently used semiconductor laser beam.

SUMMARY OF THE INVENTION

Accordingly, a first object of the present invention is to provide an electrophotographic photoconductor capable of showing flat and high sensitivity over a wide wavelength range from the visible light range to the near infrared range so as to cope with a digital copying machine and a digital printer.

A second object of the present invention is to provide a bisazo compound useful as an organic photoconductive material in the electrophotographic photoconductor which has high sensitivity and can be put to practical use in the laser printer as well as the high-speed copying machine.

A third object of the present invention is to provide a method of preparing the above-mentioned bisazo compound.

A fourth object of the present invention is to provide raw materials for the preparation of the above-mentioned bisazo compound.

A fifth object of the present invention is to provide a method of preparing each of the above-mentioned raw materials.

The first object of the present invention can be achieved by an electrophotographic photoconductor comprising an electroconductive support, and a photoconductive layer formed thereon which comprises as the effective component at least one bisazo compound of formula (I):

(I)

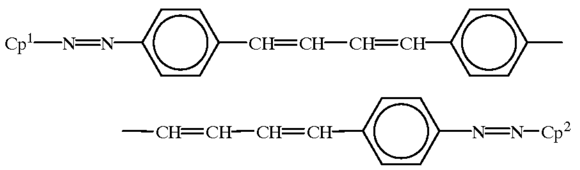

wherein $Cp^1$ and $Cp^2$ are each a coupler radical which may be the same or different.

The-second object of the present invention can be achieved by a bisazo compound of formula (II):

(II)

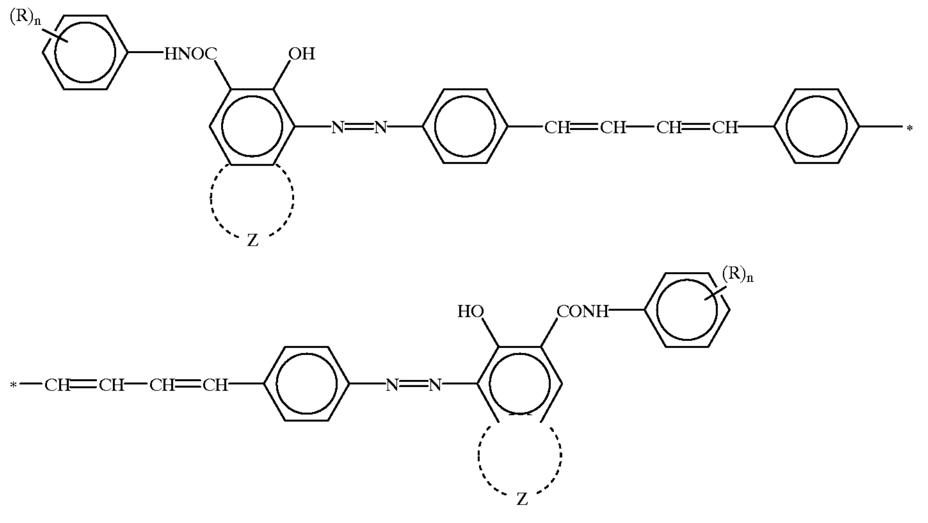

wherein Z is a benzene ring, a naphthalene ring or a carbazole ring, each of which may have a substituent; R is independently a hydrogen atom, a halogen atom, a lower alkyl group, a lower alkoxyl group or nitro group; n is an integer of 1, 2 or 3.

The third object of the present invention can be achieved by a method of producing the bisazo compound of formula (II) comprising the step of allowing a bis(diazonium salt) compound of formula (III) to react with a coupler of formula (IV):

(III)

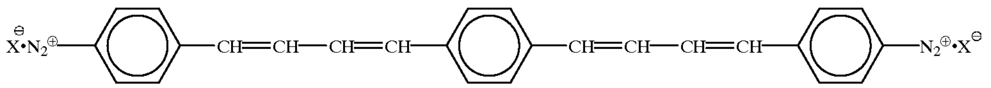

wherein X is an anionic functional group; and (IV)

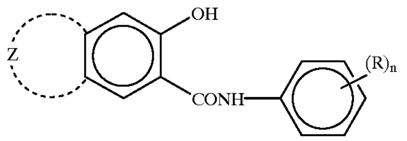

wherein Z is a benzene ring, a naphthalene ring or a carbazole ring, each of which may have a substituent; R is independently a hydrogen atom, a halogen atom, a lower alkyl group, a lower alkoxyl group or nitro group; and n is an integer of 1, 2 or 3.

The fourth object of the present invention can be achieved by (i) 1,4-bis[4-(4-nitrophenyl)-1,3-butadienyl]benzene represented by formula (V):

(V)

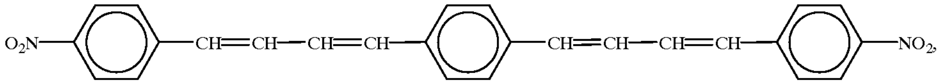

(ii) 1,4-bis[4-(4-aminophenyl)-1,3-butadienyl]benzene represented by formula (VI):

(VI)

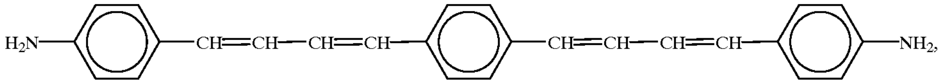 and (iii) a bis(diazonium salt) compound represented by formula (III):

(III)

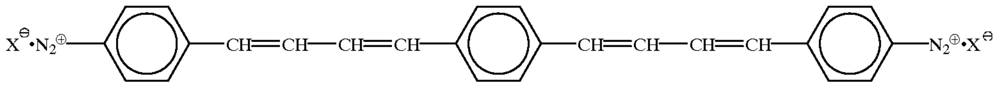

wherein X is an anionic functional group.

The fifth object of the present invention can be achieved by a method of producing 1,4-bis[4-(4-nitrophenyl)-1,3-butadienyl]benzene of formula (V) comprising the step of allowing a bis(phosphonium salt) compound of formula (VII) to react with 4-nitrocinnamaldehyde:

(VII)

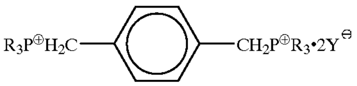

wherein R is phenyl group or an alkyl group; and $Y^{\ominus}$ is a halogen ion.

The fifth object of the present invention can also be achieved by a method of producing 1,4-bis[4-(4-nitrophenyl)-1,3-butadienyl]benzene of formula (V) comprising the step of allowing a phosphonate of formula (VIII) to react with terephthalaldehyde:

(VIII)

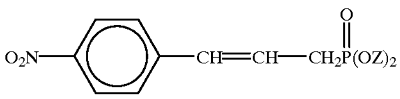

wherein Z is a lower alkyl group.

Further, the fifth object of the present invention can be achieved by a method of producing 1,4-bis[4-(4-aminophenyl)-1,3-butadienyl]benzene of formula (VI) comprising the step of reducing 1,4-bis[4-(4-nitrophenyl)-1,3-butadienyl]benzene of formula (V).

Furthermore, the fifth object of the present invention can be achieved by a method of producing a bis(diazonium salt) compound of formula (III) comprising the step of subjecting 1,4-bis[4-(4-aminophenyl)-1,3-butadienyl]benzene of formula (VI) to diazotization.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
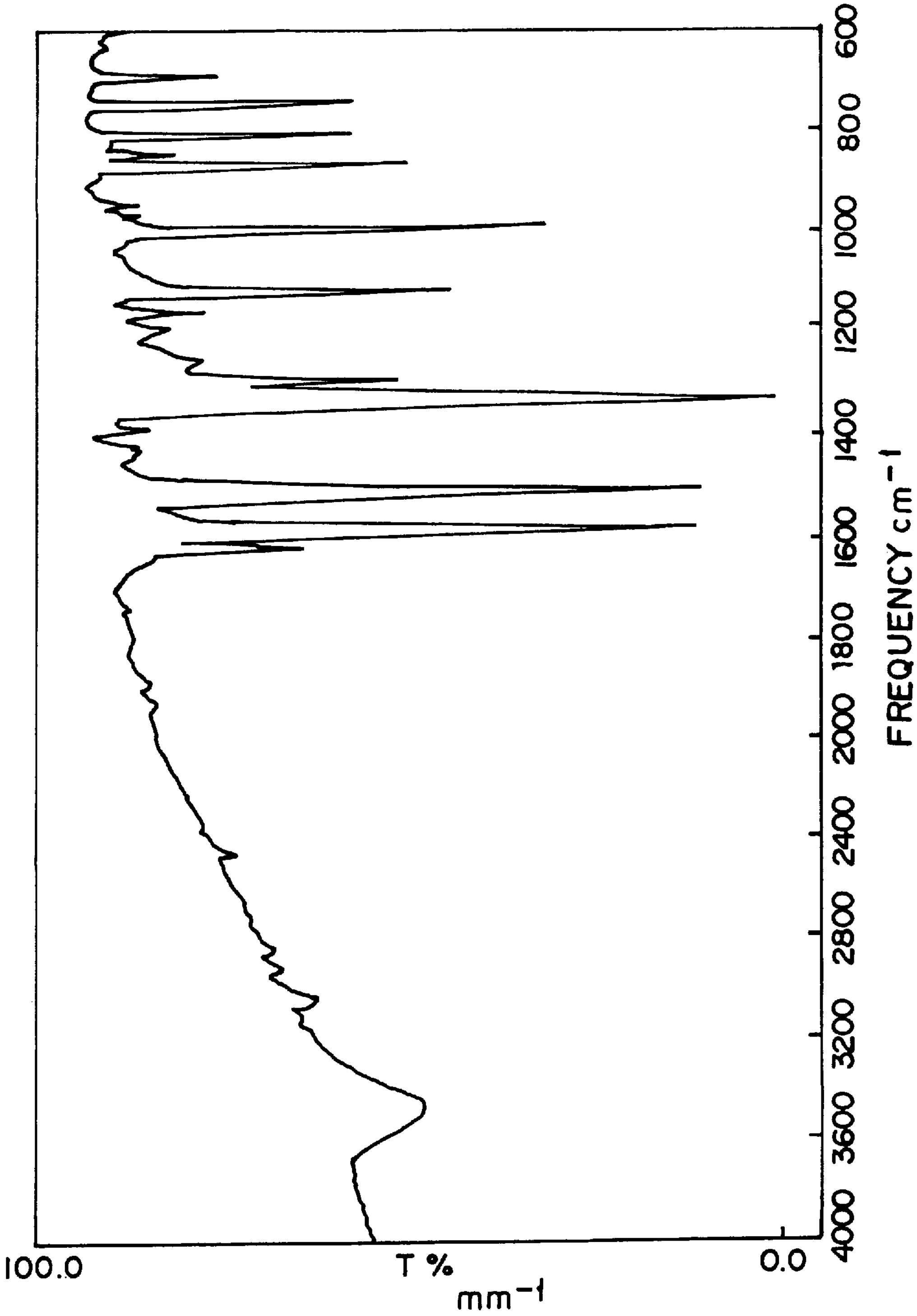
FIG. 1 is an IR spectrum of 1,4-bis[4-( 4-nitrophenyl)-1,3-butadienyl]benzene according to the present invention, which is obtained in Synthesis Example 1.

An electrophotographic photoconductor according to the present invention comprises an electroconductive support, and a photoconductive layer formed thereon which comprises at least one bisazo compound of formula (I):

(I)

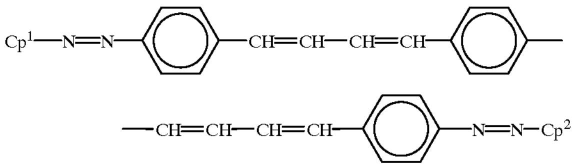

wherein $Cp^1$ and $Cp^2$ are each a coupler radical which may be the same or different.

The bisazo compound of formula (I) can be obtained by the reaction between a bis(diazonium salt) compound of the following formula (III) and couplers represented by ($Cp^1$-H) and ($Cp^2$-H).

(III)

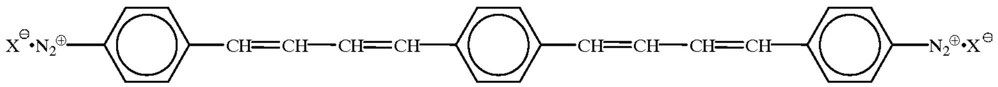

wherein X is an anionic functional group.

Examples of the anionic functional group represented by X in formula (III) are $Cl^-$, $Br^-$, $I^-$, $BF_4^-$, $PF_6^-$, $B(C_6H_5)_4^-$, $ClO_4^-$, $SO_4^{2-}$,

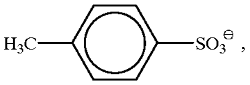

$AsF_6^-$, and $SbF_6^-$. In particular, $BF_4^-$ is preferable as the anionic functional group.

To synthesize a bisazo compound of formula (I) having different coupler radicals of $Cp^1$ and $Cp^2$, one mole of the previously mentioned bis(diazonium salt) of formula (III) and one mole of one coupler are subjected to coupling reaction, and thereafter, the coupling reaction of one mole of the bis(diazonium salt) compound with one mole of the other coupler is carried out. Alternatively, a corresponding diamine compound is subjected to diazotization, with one amino group of the diamine compound being protected, for example, with acetyl group, followed by the coupling reaction with one of the couplers. Then, the obtained compound is subjected to hydrolysis, for example, using hydrochloric acid so that the acetyl group may be replaced by the amino group. The diamine compound is thus subjected to diazotization again, followed by the coupling reaction with the other coupler.

Examples of the couplers represented by ($Cp^1$-H) and ($Cp^2$-H) used for the preparation of the bisazo compound of formula (I) include an aromatic hydrocarbon compound having hydroxyl group and a heterocyclic compound having hydroxyl group, such as phenols and naphthols; an aromatic hydrocarbon compound having amino group and a heterocyclic compound having amino group; an aromatic hydrocarbon compound having hydroxyl group and amino group and a heterocyclic compound having hydroxyl group and amino group, such as aminonaphthols; and an aliphatic or aromatic compound having a ketone group of enol form, that is, a compound with an active methylene group.

As the preferable examples of the coupler radicals represented by $Cp^1$ and $Cp^2$, the following coupler radicals (A) to (O) can be employed:

(A)

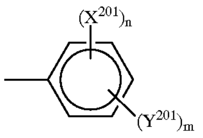

-continued (B)

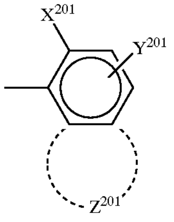

(C)

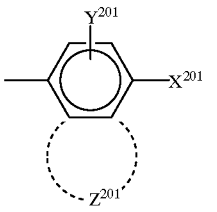

(D)

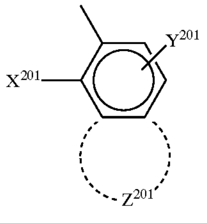

wherein:

$X^{201}$ is —OH, —$N(R^{201})(R^{202})$ or —$NHSO_2$—$R^{203}$, in which $R^{201}$ and $R^{202}$ are each hydrogen atom, or a substituted or unsubstituted alkyl group; and $R^{203}$ is a substituted or unsubstituted alkyl group or a substituted or unsubstituted aryl group;

$Y^{201}$ is hydrogen atom, a halogen atom, a substituted or unsubstituted alkyl group, a substituted or unsubstituted alkoxyl group, carboxyl group, sulfone group, a substituted or unsubstituted sulfamoyl group, or —$CON(R^{204})(Y^{202})$, in which $R^{204}$ is hydrogen atom, a substituted or unsubstituted alkyl group, or a substituted or unsubstituted phenyl group; and $Y^{202}$ is a substituted or unsubstituted cyclic hydrocarbon group, a substituted or unsubstituted heterocyclic group, or $—N{=}C(R^{205})(R^{206})$, in which $R^{205}$ is a substituted or unsubstituted cyclic hydrocarbon group, a substituted or unsubstituted heterocyclic group, or substituted or unsubstituted styryl group; and $R^{206}$ is hydrogen atom, a substituted or unsubstituted alkyl group, or a substituted or unsubstituted phenyl group, and $R^{205}$ and $R^{206}$ may form a ring together with the carbon atom bonded thereto;

$Z^{201}$ is a substituted or unsubstituted cyclic hydrocarbon ring, or a substituted or unsubstituted heterocyclic ring;

n is an integer of 1 or 2; and m is an integer of 1 or 2.

(E)

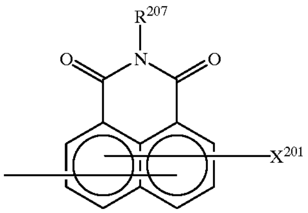

wherein $R^{207}$ is a substituted or unsubstituted hydrocarbon group; and $X^{201}$ is the same as that previously defined.

(F)

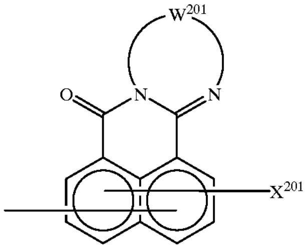

wherein $W^{201}$ is a bivalent aromatic hydrocarbon group or a bivalent heterocyclic group containing nitrogen atom therein, and the ring may have a substituent; and $X^{201}$ is the same as that previously defined.

(G)

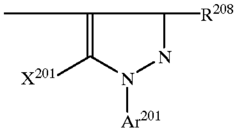

wherein $R^{208}$ is an alkyl group, carbamoyl group, or carboxyl group or an ester group thereof; $Ar^{201}$ is a substituted or unsubstituted cyclic hydrocarbon group; and $X^{201}$ is the same as that previously defined.

(H)

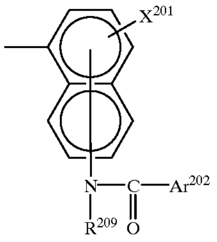

(J)

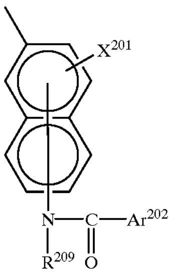

wherein $R^{209}$ is hydrogen atom, or a substituted or unsubstituted hydrocarbon group; $Ar^{202}$ is a substituted or unsubstituted cyclic hydrocarbon group; and $X^{201}$ is the same as that previously defined.

In the previously mentioned coupler radicals of formulas (B), (C) and (D), $Z^{201}$ represents a hydrocarbon ring such as benzene ring or naphthalene ring; or a heterocyclic ring such as indole ring, carbazole ring, benzofuran ring or dibenzofuran ring. The ring represented by $Z^{201}$ may have as a substituent a halogen atom, such as chlorine atom or bromine atom.

In the formulas (A) to (D), specific examples of the cyclic hydrocarbon group represented by $Y^{202}$ or $R^{205}$ include phenyl group, naphthyl group, anthryl group, and pyrenyl group; and specific examples of the heterocyclic group represented by $Y^{202}$ or $R^{205}$ include pyridyl group, thienyl group, furyl group, indolyl group, benzofuranyl group, carbazolyl group, and dibenzofuranyl group. Further, $R^{205}$ and $R^{206}$ may form in combination a ring such as fluorene ring. Specific examples of the substituent for the cyclic hydrocarbon group or heterocyclic group represented by $Y^{202}$ or $R^{205}$, or the substituent for the ring formed by the combination of $R^{205}$ and $R^{206}$ include an alkyl group such as methyl group, ethyl group, propyl group or butyl group; an alkoxyl group such as methoxy group, ethoxy group, propoxy group or butoxy group; a halogen atom such as chlorine atom or bromine atom; a dialkylamino group such as dimethylamino group or diethylamino group; a halomethyl group such as trifluoromethyl group; nitro group; cyano group; carboxyl group and an ester group thereof; hydroxyl group; and a sulfonate group such as $—SO_3Na$.

As a substituent for the phenyl group represented by $R^{204}$, there can be employed a halogen atom such as chlorine atom or bromine atom.

As the hydrocarbon group represented by $R^{207}$ or $R^{209}$ in the formulas (E), (H) and (J), there can be employed the following groups: (i) an alkyl group such as methyl group, ethyl group, propyl group or butyl group, which may have a substituent selected from the group consisting of an alkoxyl group such as methoxy group, ethoxy group, propoxy group or butoxy group, a halogen atom such as chlorine atom or bromine atom, hydroxyl group and nitro group; and (ii) an aryl group such as phenyl group, which may have a substituent selected from the group consisting of an alkyl group such as methyl group, ethyl group, propyl group or butyl group; an alkoxyl group such as methoxy group, ethoxy group, propoxy group or butoxy group, a halogen atom such as chlorine atom or bromine atom, hydroxyl group and nitro group.

Examples of the cyclic hydrocarbon group represented by $Ar^{201}$ or $Ar^{202}$ in formulas (G), (H) and (J) are phenyl group and naphthyl group. Examples of the substituent for the cyclic hydrocarbon group represented by $Ar^{201}$ or $Ar^{202}$ are an alkyl group such as methyl group, ethyl group, propyl group or butyl group; an alkoxyl group such as methoxy group, ethoxy group, propoxy group or butoxy group; nitro group; a halogen atom such as chlorine atom or bromine atom; cyano group; and a dialkylamino group such as dimethylamino group or diethylamino group.

In the coupler radicals (A) to (J), hydroxyl group is particularly preferable as the group represented by $X^{201}$.

Of the above-mentioned coupler radicals, the coupler radicals of formulas (B), (E), (F), (G), (H) and (J) are preferable in the present invention, and in particular, it is more preferable that $X^{201}$ in each coupler radical represent hydroxyl group.

To be more specific, the following coupler radical of formula (K) is preferable, and that of formula (L) is more preferable:

(K)

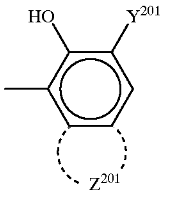

wherein $Y^{201}$ and $Z^{201}$ are the same as those previously defined.

(L)

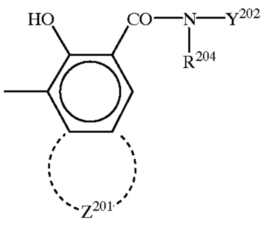

wherein $Z^{201}$, $Y^{202}$, and $R^{204}$ are the same as those previously defined.

Furthermore, the following coupler radicals of formulas (M) and (N) are particularly preferable:

(M)

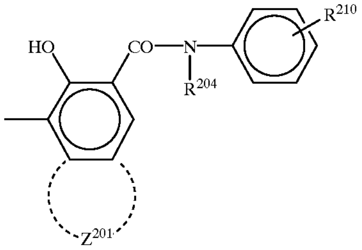

(N)

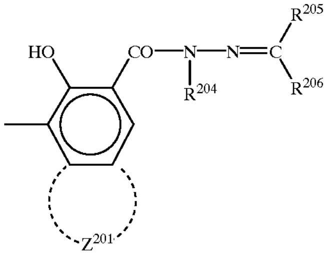

wherein $Z^{201}$, $R^{204}$, $R^{205}$ and $R^{206}$ are the same as those previously defined; and $R^{210}$ represents the same substituents as those for $Y^{202}$.

In addition, the following coupler radical represented by formula (O) is also preferable in the present invention.

(O)

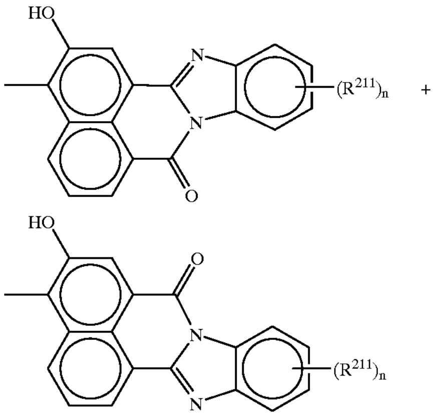

wherein $R^{211}$ is hydrogen atom, an alkyl group, an alkoxyl group, or a halogen atom; and n is an integer of 1 to 4.

In the formula (O), examples of the alkyl group represented by $R^{211}$ are methyl group, ethyl group, propyl group and butyl group. Examples of the alkoxyl group represented by $R^{211}$ are methoxy group, ethoxy group, propoxy group and butoxy group. Examples of the halogen atom represented by $R^{211}$ are chlorine atom, bromine atom and fluorine atom.

Specific examples of the coupler of ($Cp^1$-H) or ($Cp^2$-H), which is used for the preparation of the bisazo compound of formula (I) are shown in TABLE 1 to TABLE 14.

TABLE 1

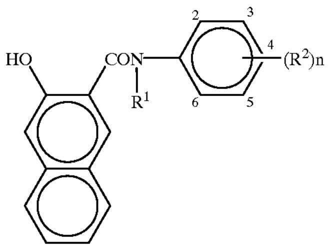

| Coupler No. | $R^1$ | $(R^2)_n$ | Melting Point (° C.) |
|---|---|---|---|
| 1 | H | H | 243–244 |
| 2 | H | $2\text{-}NO_2$ | 194–196 |
| 3 | H | $3\text{-}NO_2$ | 246–247 |
| 4 | H | $4\text{-}NO_2$ | 266–267.5 |
| 5 | H | $2\text{-}CF_3$ | 178–179 |
| 6 | H | $3\text{-}CF_3$ | 237.5–238.5 |
| 7 | H | $4\text{-}CF_3$ | 279–281 |
| 8 | H | 2-CN | 221–222.5 |
| 9 | H | 3-CN | 256.5–258.5 |
| 10 | H | 4-CN | 274.5–277 |
| 11 | H | 2-I | 199–199.5 |
| 12 | H | 3-I | 258.5–259.5 |
| 13 | H | 4-I | 261.5–262 |
| 14 | H | 2-Br | 217–218 |
| 15 | H | 3-Br | 254–255 |
| 16 | H | 4-Br | 265–268 |
| 17 | H | 2-Cl | 228–230 |
| 18 | H | 3-Cl | 256.5–257 |
| 19 | H | 4-Cl | 264–266 |
| 20 | H | 2-F | 223.0–224.0 |
| 21 | H | 3-F | 250.0–251.0 |
| 22 | H | 4-F | 265.0–267.0 |
| 23 | H | $2\text{-}CH_3$ | 195.5–198.0 |
| 24 | H | $3\text{-}CH_3$ | 214.5–216.5 |
| 25 | H | $4\text{-}CH_3$ | 227.0–229.0 |
| 26 | H | $2\text{-}C_2H_5$ | 168.5–169.5 |
| 27 | H | $4\text{-}C_2H_5$ | 203.0–204.5 |
| 28 | H | $2\text{-}OCH_3$ | 167–168 |
| 29 | H | $3\text{-}OCH_3$ | 195.5–198.0 |
| 30 | H | $4\text{-}OCH_3$ | 229–230 |
| 31 | H | $2\text{-}OC_2H_5$ | 157–158 |
| 32 | H | $3\text{-}OC_2H_5$ | 188.5–189.0 |
| 33 | H | $4\text{-}OC_2H_5$ | 225.0–225.5 |
| 34 | H | $4\text{-}N(CH_3)_2$ | 232.0–233.5 |
| 35 | $—CH_3$ | H | 189.5–190.5 |
| 36 | 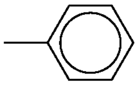 | H | 182.0–183.0 |
| 37 | H | $2\text{-}OCH_3$, $5\text{-}OCH_3$ | 186.0–188.0 |
| 38 | H | $2\text{-}OC_2H_5$, $5\text{-}OC_2H_5$ | 173.0–173.5 |
| 39 | H | $2\text{-}CH_3$, $5\text{-}CH_3$ | 207.0–208.5 |
| 40 | H | 2-Cl, 5-Cl | 253.5–254.5 |
| 41 | H | $2\text{-}CH_3$, 5-Cl | 245–247 |
| 42 | H | $2\text{-}OCH_3$, $4\text{-}OCH_3$ | 151.0–152.0 |
| 43 | H | $2\text{-}CH_3$, $4\text{-}CH_3$ | 226–228 |
| 44 | H | $2\text{-}CH_3$, 4-Cl | 244–245 |
| 45 | H | $2\text{-}NO_2$, $4\text{-}OCH_3$ | 179.5–181.0 |
| 46 | H | $3\text{-}OCH_3$, $5\text{-}OCH_3$ | 180.5–182.0 |
| 47 | H | $2\text{-}OCH_3$, 5-Cl | 219.0–220.0 |
| 48 | H | $2\text{-}OCH_3$, $5\text{-}OCH_3$, 4-Cl | 193.5–195.5 |
| 49 | H | $2\text{-}OCH_3$, $4\text{-}OCH_3$, 5-Cl | 193–194 |
| 50 | H | 3-Cl, 4-Cl | 272.5–273.5 |
| 51 | H | 2-Cl, 4-Cl, 5- | 257.5–258.5 |
| 52 | H | $2\text{-}CH_3$, 3-Cl | 227.5–228.5 |
| 53 | H | 3-Cl, $4\text{-}CH_3$ | 259.5–260.5 |
| 54 | H | 2-F, 4-F | 246.0–246.5 |
| 55 | H | 2-F, 5-F | 259.0–260.0 |

TABLE 1-continued

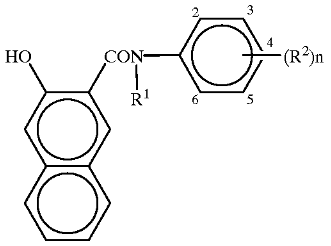

| Coupler No. | $R^1$ | $(R^2)_n$ | Melting Point (° C.) |
|---|---|---|---|
| 56 | H | 2-Cl, $4\text{-}NO_2$ | 283.0–284.0 |
| 57 | H | $2\text{-}NO_2$, 4-Cl | 226.5–227.5 |
| 58 | H | 2-Cl, 3-Cl, 4-Cl, 5-Cl | 280.0–281.5 |
| 59 | H | 4-OH | 268 |

TABLE 2

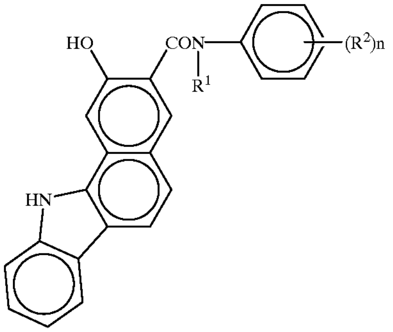

| Coupler No. | $R^1$ | $(R^2)_n$ | Melting Point (° C.) |
|---|---|---|---|
| 60 | H | H | >300 |
| 61 | H | $2\text{-}NO_2$ | 283–284 |
| 62 | H | $3\text{-}NO_2$ | >300 |
| 63 | H | $4\text{-}NO_2$ | >300 |
| 64 | H | 2-Cl | >300 |
| 65 | H | 3-Cl | >300 |
| 66 | H | 4-Cl | >300 |
| 67 | H | $2\text{-}CH_3$ | >300 |
| 68 | H | $3\text{-}CH_3$ | >300 |
| 69 | H | $4\text{-}CH_3$ | >300 |
| 70 | H | $2\text{-}C_2H_5$ | 271–273 |
| 71 | H | $4\text{-}C_2H_5$ | >300 |
| 72 | H | $2\text{-}OCH_3$ | 276–278 |
| 73 | H | $3\text{-}OCH_3$ | >300 |
| 74 | H | $4\text{-}OCH_3$ | >300 |
| 75 | H | $2\text{-}OC_2H_5$ | 273.5–275.0 |
| 76 | H | $4\text{-}OC_2H_5$ | >300 |
| 77 | H | $2\text{-}CH_3$, $4\text{-}OCH_3$ | 296 |
| 78 | H | $2\text{-}CH_3$, $4\text{-}CH_3$ | >300 |
| 79 | H | $2\text{-}CH_3$, $5\text{-}CH_3$ | 274.0–276.0 |
| 80 | H | $2\text{-}CH_3$, $6\text{-}CH_3$ | >300 |
| 81 | H | $2\text{-}OCH_3$, $4\text{-}OCH_3$ | 296.5–298.5 |
| 82 | H | $2\text{-}OCH_3$, $5\text{-}OCH_3$ | 284.5–286.5 |
| 83 | H | $3\text{-}OCH_3$, $5\text{-}OCH_3$ | 300.5–302.0 |
| 84 | H | $2\text{-}CH_3$, 3-Cl | 296.0–297.5 |
| 85 | H | $2\text{-}CH_3$, 4-Cl | >300 |
| 86 | H | $2\text{-}CH_3$, 5-Cl | 290.5–292.0 |

TABLE 2-continued
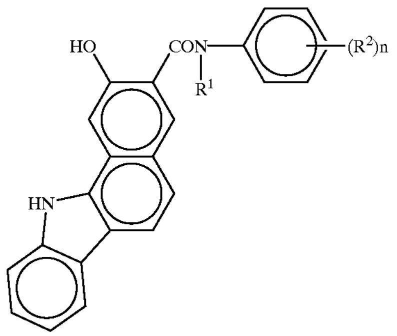
| Coupler No. | $R^1$ | $(R^2)_n$ | Melting Point (° C.) |
|---|---|---|---|
| 87 | H | 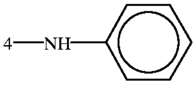 | 304 |
| 88 | H | 2-$CH(CH_3)_2$ | 239.0–240.0 |
TABLE 3
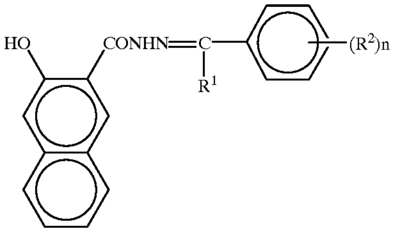
| Coupler No. | $R^1$ | $(R^2)_n$ | Melting Point (° C.) |
|---|---|---|---|
| 89 | H | H | 228.0–230.0 |
| 90 | H | 4-$N(CH_3)_2$ | 238.5–240.0 |
| 91 | H | 2-$OCH_3$ | 218.0–222.0 |
| 92 | H | 3-$OCH_3$ | 186.5–188.5 |
| 93 | H | 4-$OCH_3$ | 224.5–225.0 |
| 94 | H | 4-$OC_2H_5$ | 236.0–237.5 |
| 95 | H | 2-$CH_3$ | 227.0–228.0 |
| 96 | H | 3-$CH_3$ | 212.5–214.0 |
| 97 | H | 4-$CH_3$ | 233.0–236.0 |
| 98 | H | 2-F | 233.0–233.5 |
| 99 | H | 3-F | 248.5 |
| 100 | H | 4-F | 239. 5–240.0 |
| 101 | H | 2-Cl | 254.0–255.0 |
| 102 | H | 3-Cl | 226.5–230.0 |
| 103 | H | 4-Cl | 265.5–269.0 |
| 104 | H | 2-Br | 243.0 |
| 105 | H | 3-Br | 231.0–231.5 |
| 106 | H | 4-Br | 259.0 |
| 107 | H | 2-Cl, 4-Cl | 251.5–252.0 |
| 108 | H | 3-Cl, 4-Cl | 260.0–261.0 |
| 109 | H | 2-CN | 175.0–176.5 |
| 110 | H | 4-CN | 267.5–268.0 |
| 111 | H | 2-$NO_2$ | 240.0 |
| 112 | H | 3-$NO_2$ | 255.5–257.0 |
| 113 | H | 4-$NO_2$ | 260.0–261.0 |

TABLE 3-continued
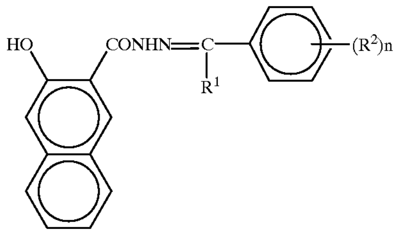
| Coupler No. | $R^1$ | $(R^2)_n$ | Melting Point (° C.) |
| --- | --- | --- | --- |
| 114 | H | 2-$CH_3$, 4-$CH_3$ | 234.5–236.5 |
| 115 | H | 2-$OCH_3$, 5-$OCH_3$ | 221.5–222.0 |
| 116 | H | 2-$OCH_3$, 3-$OCH_3$, 4-$OCH_3$ | 191.0–192.0 |
| 117 | —$CH_3$ | H | 248.5–250.0 |
| 118 | 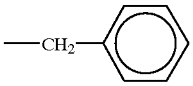 | H | 182.5–185.0 |
| 119 | 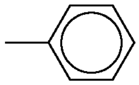 | H | 213.0–214.5 |
| 120 | H | 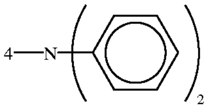 | 237.0–237.5 |
TABLE 4
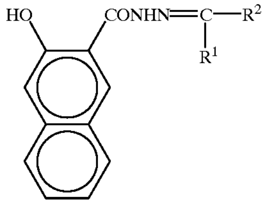
| Coupler No. | $R^1$ | $R^2$ | Melting Point (° C.) |
| --- | --- | --- | --- |
| 121 | —$CH_3$ | —$CH_3$ | 232.5–233.0 |
| 122 | H | 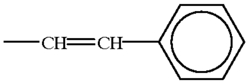 | 208.5–209.0 |
| 123 | H | 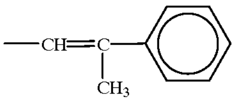 | 224.0–224.5 |
| 124 | H | 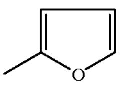 | 197.5–199.0 |
| 125 | H | 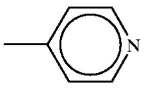 | 188.0–188.5 |
TABLE 4-continued
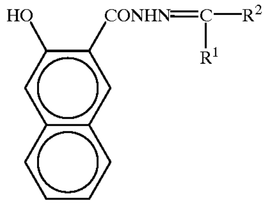
| Coupler No. | $R^1$ | $R^2$ | Melting Point (° C.) |
| --- | --- | --- | --- |
| 126 | H | 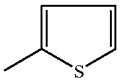 | 227.0–228.0 |
| 127 | —$CH_3$ | 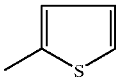 | 225.5–226.0 |
| 128 | H | 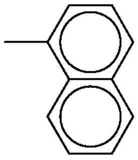 | 212.5–214.0 |

TABLE 4-continued
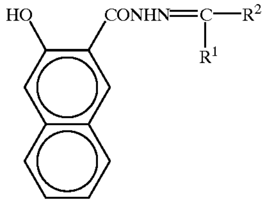
| Coupler No. | $R^1$ | $R^2$ | Melting Point (° C.) |
|---|---|---|---|
| 129 | H | 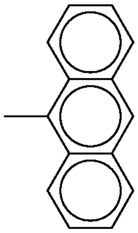 | 257 |
| 130 | H | 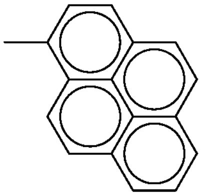 | 250 |
| 131 | H | 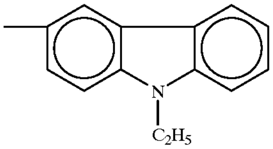 | 232.5–236.0 |
| 132 | H | 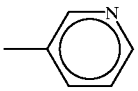 | 240.5–241.5 |
TABLE 5
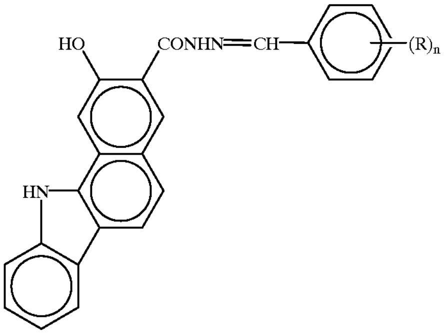
| Coupler No. | $(R)_n$ | Melting Point (° C.) |
|---|---|---|
| 133 | H | >300 |
| 134 | 2-$OCH_3$ | 268 |
| 135 | 3-$OCH_3$ | 281.0–283.0 |
| 136 | 4-$OCH_3$ | 293 |
| 137 | 2-$CH_3$ | 297 |
| 138 | 3-$CH_3$ | 296 |
TABLE 5-continued
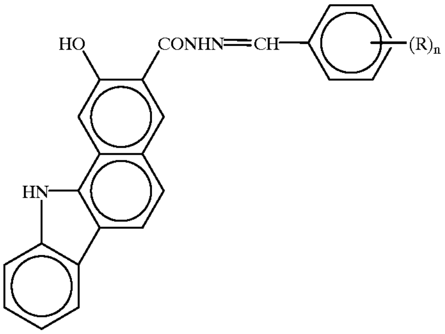
| Coupler No. | $(R)_n$ | Melting Point (° C.) |
|---|---|---|
| 139 | 4-$CH_3$ | >300 |
| 140 | 4-Cl | >300 |
| 141 | 2-$NO_2$ | >300 |
| 142 | 4-$NO_2$ | >300 |
| 143 | 2-OH | >300 |
| 144 | 2-OH, 3-$NO_2$ | >300 |
| 145 | 2-OH, 5-$NO_2$ | >300 |
| 146 | 2-OH, 3-$OCH_3$ | >300 |
TABLE 6
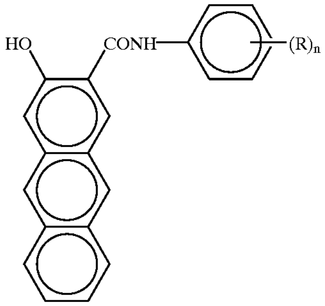
| Coupler No. | $(R)_n$ | Melting Point (° C.) |
|---|---|---|
| 147 | 4-Cl | >300 |
| 148 | 2-$NO_2$ | 268–274 |
| 149 | 3-$NO_2$ | >300 |
| 150 | 4-$NO_2$ | >300 |
| 151 | 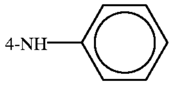 | 296 |
| 152 | H | 300–307 |
| 153 | 2-$OCH_3$ | 242–248 |
| 154 | 3-$OCH_3$ | 269–275 |
| 155 | 4-$OCH_3$ | 312 |
| 156 | 2-$CH_3$ | 265–270 |
| 157 | 3-$CH_3$ | 270–278 |
| 158 | 4-$CH_3$ | 304 |
| 159 | 2-Cl | 283–288 |
| 160 | 3-Cl | 281–287 |

TABLE 7
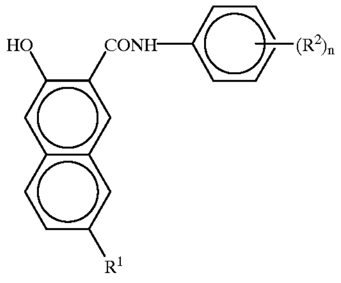
| Coupler No. | $R^1$ | $(R^2)_n$ | Melting Point (° C.) |
|---|---|---|---|
| 161 | H | 2-$OCH_3$, 4-Cl, 5-$CH_3$ | 208.0–208.5 |
| 162 | —$OCH_3$ | H | 230.5–231.5 |
| 163 | —$OCH_3$ | 2—$CH_3$ | 205.5–206.0 |
| 164 | —$OCH_3$ | 2-$OCH_3$, 5-$OCH_3$, 4-Cl | 245.5–246.0 |
TABLE 8
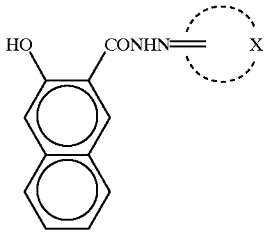
| Coupler No. | X | Melting Point (° C.) |
|---|---|---|
| 165 | 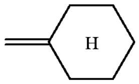 | 207.0–209.0 |
| 166 | 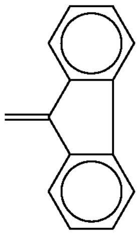 | 257.0–259.0 |
TABLE 8-continued
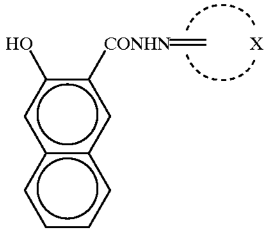
| Coupler No. | X | Melting Point (° C.) |
|---|---|---|
| 167 | 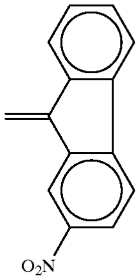 | 290 |
TABLE 9
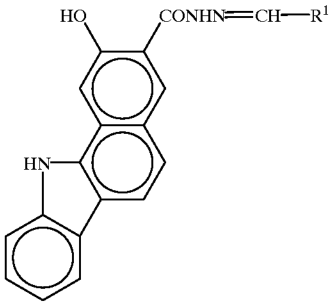
| Coupler No. | $R^1$ | Melting Point (° C.) |
|---|---|---|
| 168 | 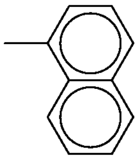 | >300 |
| 169 | 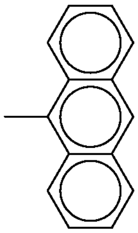 | >300 |

TABLE 9-continued
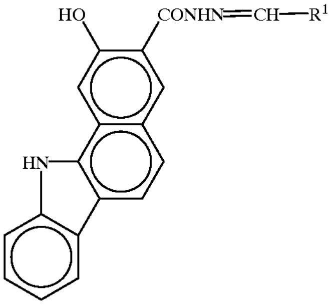
| Coupler No. | $R^1$ | Melting Point (° C.) |
|---|---|---|
| 170 | 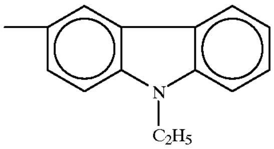 | >300 |
| 171 | 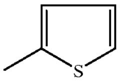 | 298 |
TABLE 10
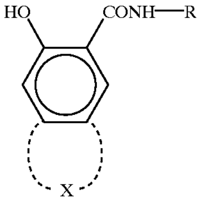
| Coupler No. | X | R | Melting Point (° C.) |
|---|---|---|---|
| 172 | 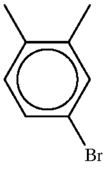 | 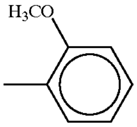 | 180–183 |
| 173 | 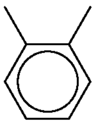 | 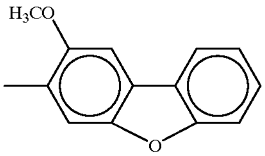 | 228.5–229.5 |
| 174 | 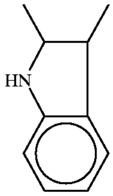 | 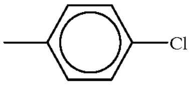 | >262 |
TABLE 10-continued
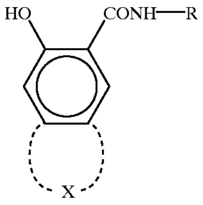
| Coupler No. | X | R | Melting Point (° C.) |
|---|---|---|---|
| 175 | 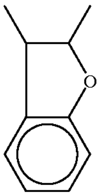 | 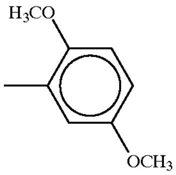 | 226.5–227.0 |
| 176 | 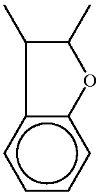 | 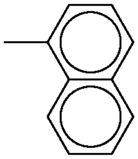 | 308–310 |
| 177 | 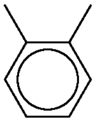 | 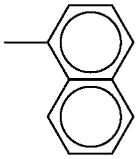 | 222–223 |
TABLE 11
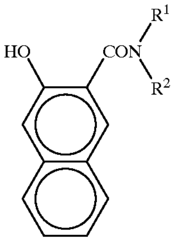
| Coupler No. | $R^1$ | $R^2$ | Melting Point (° C.) |
|---|---|---|---|
| 178 | H | H | 220.5–221.5 |
| 179 | $—CH_3$ | H | 190.5–192.5 |
| 180 | $—CH_3$ | $—CH_3$ | 196.0–198.0 |
| 181 | H | 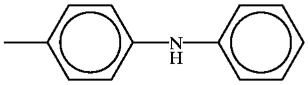 | 222.0–223.0 |

TABLE 12
| Coupler No. | Structure | Melting Point (° C.) |
|---|---|---|
| 182 | 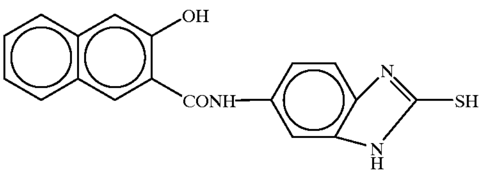 | >300 |
| 183 | 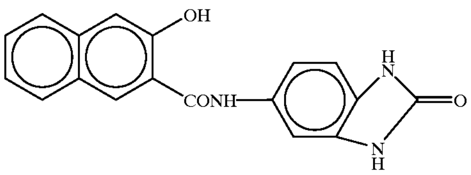 | >300 |
| 184 | 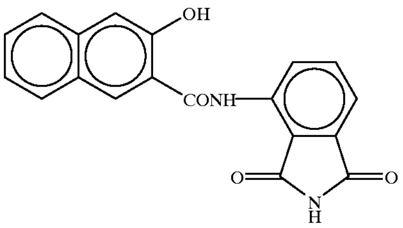 | >300 |
| 185 | 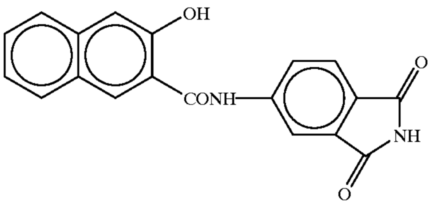 | >300 |
| 186 | 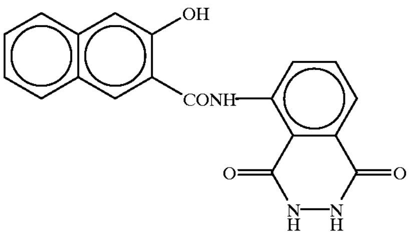 | >300 |
| 187 | 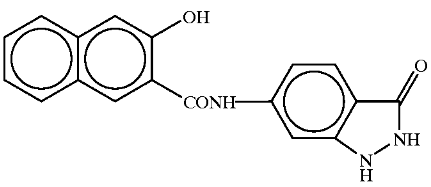 | >300 |
| 188 | 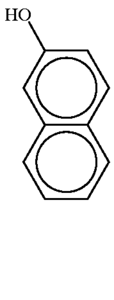 | 122.0–122.5 |

TABLE 12-continued
| Coupler No. | Structure | Melting Point (° C.) |
|---|---|---|
| 189 | 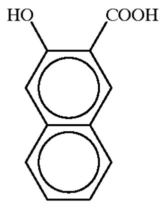 | 222.5–224.0 |
| 190 | 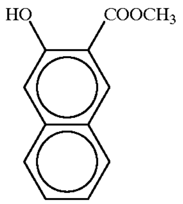 | 74.5–75.5 |
| 191 | 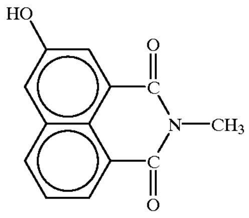 | 275.5–276.5 |
| 192 | 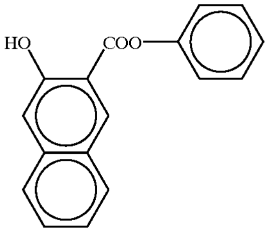 | 130.5–131.5 |
| 193 | 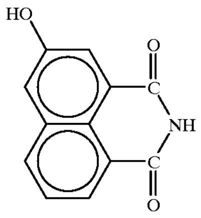 | >300 |
| 194 | 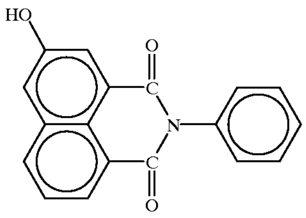 | >300 |

TABLE 12-continued
| Coupler No. | Structure | Melting Point (° C.) |
|---|---|---|
| 195 | 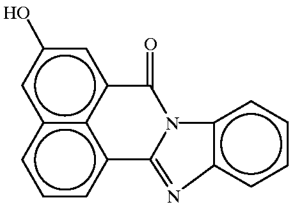 | >300 |
| 196 | 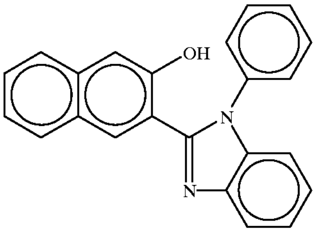 | 172.5–173.5 |
| 197 | 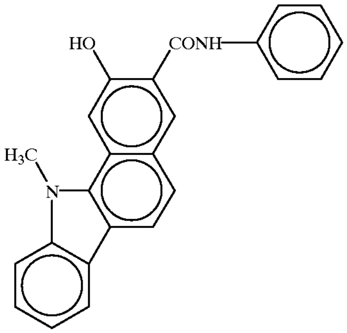 | 262.5–265.5 |
| 198 | 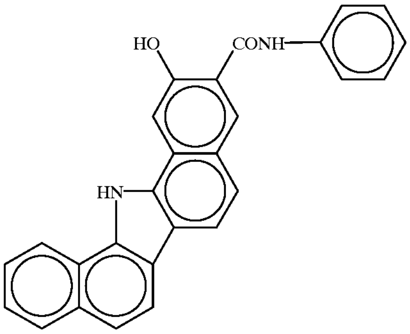 | >300 |

TABLE 12-continued

| Coupler No. | Structure | Melting Point (° C.) |
|---|---|---|
| 199 | 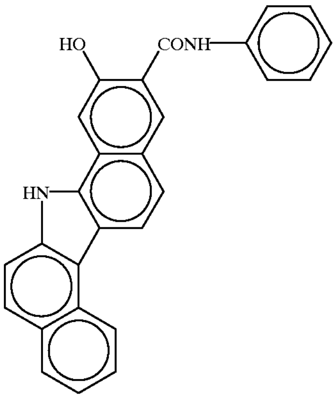 | >300 |
| 200 | 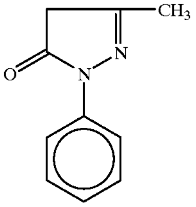 | 128.0–129.0 |

TABLE 13

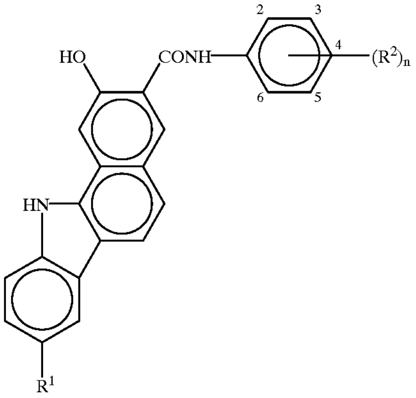

| Coupler No. | $R^1$ | $(R^2)_n$ | Melting Point (° C.) |
|---|---|---|---|
| 201 | Cl | H | >300 |
| 202 | Cl | $2\text{-}OCH_3$ | >300 |
| 203 | Cl | $3\text{-}OCH_3$ | >300 |
| 204 | Cl | $4\text{-}OCH_3$ | >300 |
| 205 | Cl | $2\text{-}CH_3$ | >300 |
| 206 | Cl | $3\text{-}CH_3$ | >300 |
| 207 | Cl | $4\text{-}CH_3$ | >300 |
| 208 | Cl | 2-Cl | >300 |
| 209 | Cl | 3-Cl | >300 |
| 210 | Cl | 4-Cl | >300 |
| 211 | Cl | $2\text{-}NO_2$ | >300 |
| 212 | Cl | $3\text{-}NO_2$ | >300 |
| 213 | Cl | $4\text{-}NO_2$ | >300 |
| 214 | Cl | $2\text{-}CH_3$, 4-Cl | >300 |
| 215 | Cl | $2\text{-}CH_3$, $4\text{-}CH_3$ | >300 |
| 216 | Cl | $2\text{-}C_2H_5$ | 299.0–301.0 |

TABLE 13-continued

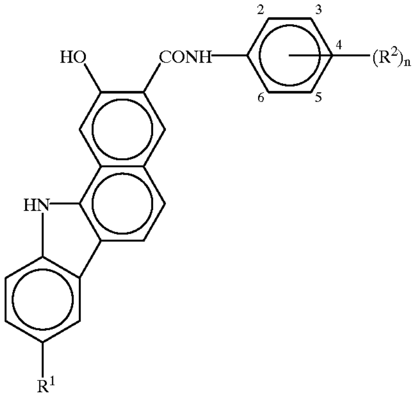

| Coupler No. | $R^1$ | $(R^2)_n$ | Melting Point (° C.) |
|---|---|---|---|
| 217 | $CH_3$ | H | >300 |
| 218 | $CH_3$ | $2\text{-}OCH_3$ | 297 |
| 219 | $CH_3$ | $3\text{-}OCH_3$ | >300 |
| 220 | $CH_3$ | $4\text{-}OCH_3$ | >300 |
| 221 | $CH_3$ | $2\text{-}CH_3$ | >300 |
| 222 | $CH_3$ | $3\text{-}CH_3$ | >300 |
| 223 | $CH_3$ | $4\text{-}CH_3$ | >300 |
| 224 | $CH_3$ | 2-Cl | >300 |
| 225 | $CH_3$ | 3-Cl | >300 |
| 226 | $CH_3$ | 4-Cl | >300 |
| 227 | $CH_3$ | $2\text{-}NO_2$ | >300 |
| 228 | $CH_3$ | $3\text{-}NO_2$ | >300 |
| 229 | $CH_3$ | $4\text{-}NO_2$ | >300 |
| 230 | $CH_3$ | $2\text{-}CH_3$, 4-Cl | >300 |
| 231 | $CH_3$ | $2\text{-}CH_3$, $4\text{-}CH_3$ | >300 |
| 232 | $CH_3$ | $2\text{-}C_2H_5$ | 268.5–270.0 |

TABLE 13-continued
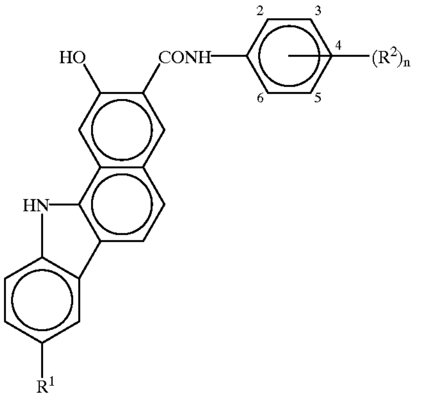
| Coupler No. | $R^1$ | $(R^2)_n$ | Melting Point (° C.) |
|---|---|---|---|
| 233 | $OCH_3$ | H | 289.0 |
| 234 | $OCH_3$ | 2-$OCH_3$ | 268.0–270.0 |
| 235 | $OCH_3$ | 3-$OCH_3$ | >300 |
| 236 | $OCH_3$ | 4-$OCH_3$ | >300 |
| 237 | $OCH_3$ | 2-$CH_3$ | 284.5–285.5 |
| 238 | $OCH_3$ | 3-$CH_3$ | >300 |
| 239 | $OCH_3$ | 4-$CH_3$ | >300 |
| 240 | $OCH_3$ | 2-Cl | >300 |
| 241 | $OCH_3$ | 3-Cl | >300 |
| 242 | $OCH_3$ | 4-Cl | >300 |
| 243 | $OCH_3$ | 2-$NO_2$ | >300 |
| 244 | $OCH_3$ | 3-$NO_2$ | >300 |
| 245 | $OCH_3$ | 4-$NO_2$ | >300 |
| 246 | $OCH_3$ | 2-$C_2H_5$ | 264.5–266.5 |
TABLE 14
| Coupler No. | Structure |
|---|---|
| 247 | 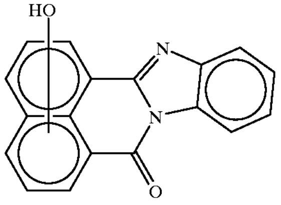 |
| 248 | 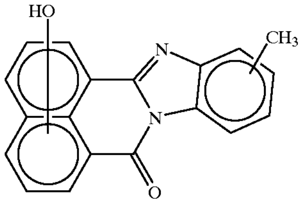 |
| 249 | 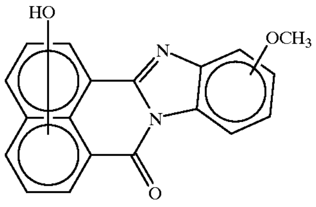 |
TABLE 14-continued
| Coupler No. | Structure |
|---|---|
| 250 | 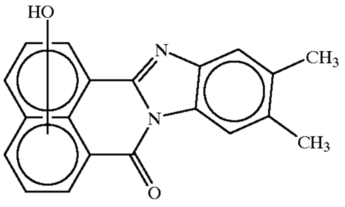 |
| 251 | 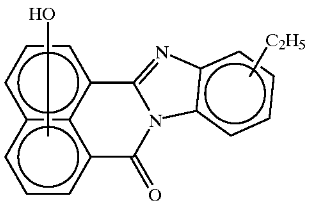 |
| 252 | 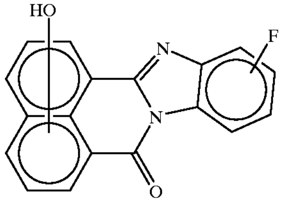 |
| 253 | 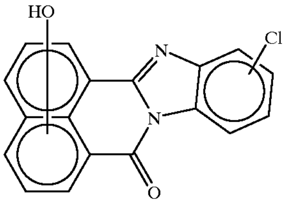 |
| 254 | 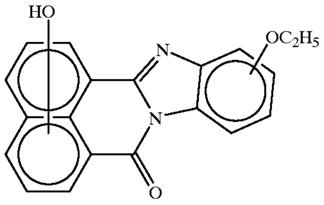 |
| 255 | 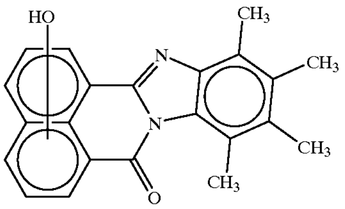 |

TABLE 14-continued

| Coupler No. | Structure |
| --- | --- |
| 256 | 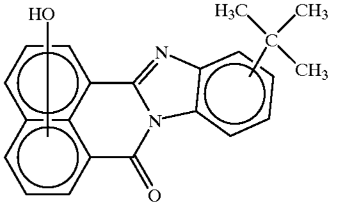 |

By using the bisazo compound of by formula (I) according to the present invention alone or in combination with a charge transport material, an electrophotographic photoconductor with a single-layered photoconductive layer or a layered photoconductive layer can be fabricated.

To fabricate the single-layered type photoconductor, a photoconductive layer in which the above-mentioned bisazo compound is dispersed alone or in combination with a charge transport material in a binder agent is provided on an electroconductive support. In the case where the layered photoconductor is fabricated, a charge generation layer comprising the bisazo compound is provided on an electroconductive support, and a charge transport layer comprising a charge transport material is overlaid on the charge generation layer. The above-mentioned overlaying order of the charge generation layer and the charge transport layer may be reversed.

For the formation of the photoconductive layer in which the above-mentioned bisazo compound is dispersed, the bisazo compound, with a binder resin being optionally added thereto, is dispersed or dissolved in an appropriate solvent, using a ball mill, ultrasonic wave, or a homomixer. Then, the above prepared coating liquid may be coated on the electroconductive support by dip coating, blade coating or spray coating, and thereafter dried.

To upgrade the dispersibility of the bisazo compound in the photoconductive layer, it is preferable that the average particle size of the bisazo compound be 2 μm or less, and more preferably 1 μm or less. Further, the average particle size of the bisazo compound may be controlled to 0.01 μm or more so as to inhibit the aggregation of fine particles. Thus, the increase of the resistivity of the photoconductive layer can be prevented and the deterioration of sensitivity and durability in the repeated use caused by the increase of defective crystallites can be prevented.

Specific examples of the solvent which is used to prepare a dispersion or solution for the photoconductive layer coating liquid include N,N-dimethylformamide, toluene, xylene, monochlorobenzene, 1,2-dichloroethane, 1,1,1-trichloroethane, dichloromethane, 1,1,2-trichloroethane, trichloroethylene, tetrahydrofuran, methyl ethyl ketone, methyl isobutyl ketone, cyclohexanone, ethyl acetate, butyl acetate and dioxane.

Any binder resin that has good electrically insulating properties and conventionally used in the preparation of the electrophotographic photoconductor can be employed for the formation of the photoconductive layer.

Specific examples of such a binder resin include addition polymerization-type resins, polyaddition-type resins and polycondensation-type resins such as polyethylene, polyvinyl butyral, polyvinyl formal, polystyrene resin, phenoxy resin, polypropylene, acrylic resin, methacrylic resin, vinyl chloride resin, vinyl acetate resin, epoxy resin, polyurethane resin, phenolic resin, polyester resin, alkyd resin, polycarbonate resin, polyamide resin, silicone resin and melamine resin; copolymer resins comprising as the repeat units two or more monomers for use in the above-mentioned resins, for example, electrically insulating resins such as vinyl chloride-vinyl acetate copolymer resin, styrene-acrylic copolymer resin and vinyl chloride-vinyl acetate-maleic anhydride copolymer resin; and a polymeric organic semiconductor such as poly-N-vinylcarbazole. Those binder resins may be used alone or in combination.

The bisazo compound of formula (I) according to the present invention may be used together with the following organic pigments: azo pigments such as C.I. Pigment Blue 25 (C.I. 21180), C.I. Pigment Red 41 (C.I. 21200), C.I. Acid Red 52 (C.I. 45100), C.I. Basic Red 3 (C.I. 45210), an azo pigment having a carbazole skeleton (Japanese Laid-Open Patent Application 53-95033), an azo pigment having a distyryl benzene skeleton (Japanese Laid-Open Patent Application 53-133445), an azo pigment having a triphenylamine skeleton (Japanese Laid-Open Patent Application 53-132347), an azo pigment having a dibenzothiophene skeleton (Japanese Laid-Open Patent Application 54-21728), an azo pigment having an oxadiazole skeleton (Japanese Laid-Open Patent Application 54-12742), an azo pigment having a fluorenone skeleton (Japanese Laid-Open Patent Application 54-22834), an azo pigment having a bisstilbene skeleton (Japanese Laid-Open Patent Application 54-17733), an azo pigment having a distyryl oxadiazole skeleton (Japanese Laid-Open Patent Application 54-2129) and an azo pigment having a distyryl carbazole skeleton (Japanese Laid-Open Patent Application 54-14967); phthalocyanine pigments such as C.I. Pigment Blue 16 (C.I. 74100) and titanyl phthalocyanine; indigo pigments such as C.I. Vat Brown 5 (C.I. 73410) and C.I. Vat Dye (C.I. 73030); and perylene pigments such as Algol Scarlet B and Indanthrene Scarlet R (made by Bayer Co., Ltd.). Two or more organic pigments mentioned above may be used in combination with the bisazo compound of formula (I).

In the layered photoconductor in which the charge generation layer and the charge transport layer are successively overlaid on the electroconductive support in this order, it is preferable that the amount of bisazo compound in the charge generation layer be 20 wt. % or more of the total weight of the binder resin for use in the charge generation layer. The thickness of the above-mentioned charge generation layer is preferably in the range of 0.01 to 5 μm. Further, in this case, it is preferable that the amount of charge transport material in the charge transport layer be in the range of 20 to 200 wt. % of the binder resin for use in the charge transport layer. The thickness of the charge transport layer is preferably in the range of 5 to 100 μm. The charge transport layer may be formed using a high-molecular weight charge transport material alone.

Further, in such a case, the addition of the charge transport material to the charge generation layer is effective for reducing the residual potential and improving the photosensitivity. When the charge transport material is added to the charge generation layer, as mentioned above, it is preferable that the amount of charge transport material be in the range of 20 to 200 wt. % of the total weight of the binder resin for use in the charge generation layer.

In the single-layered photoconductive layer, it is preferable that the amount of bisazo compound represented by formula (I) be in the range of 5 to 95 wt. % of the total weight of the binder resin for use in the photoconductive layer. In this case, the thickness of the photoconductive layer is preferably in the range of 10 to 100 μm. When the bisazo compound and a charge transport material are used in combination in the single-layered photoconductive layer, it is preferable that the amount of charge transport material be in the range of 30 to 200 wt. % of the total weight of the binder resin for use in the photoconductive layer.

For the formation of the single-layered photoconductive layer, the previously mentioned high-molecular weight charge transport material and the bisazo compound of the present invention may be used in combination. In such a case, it is preferable that the amount of bisazo compound be in the range of 5 to 95 wt. % of the total weight of the high-molecular weight charge transport material for use in the photoconductive layer, and that the thickness of the photoconductive layer be in the range of 10 to 100 μm.

To improve the chargeability, both the layered photoconductive layer and the single-layered photoconductive layer may further comprise a phenol compound, a hydroquinone compound, a hindered phenol compound, a hindered amine compound, and a compound having a hindered amine and a hindered phenol in a molecule thereof.

For the electroconductive support, there can be employed a metallic plate, drum or foil made of aluminum, nickel, copper, titanium, gold or stainless steel; a plastic film on which an electroconductive material such as aluminum, nickel, copper, titanium, gold, tin oxide or indium oxide is deposited; and a sheet of paper or a plastic film, which may be formed in a drum, coated with an electroconductive material.

The electrophotographic photoconductor of the present invention may further comprise an intermediate layer which is provided between the electroconductive support and the photoconductive layer for the purpose of increasing the adhesion between the electroconductive support and the photoconductive layer and improving the charge blocking characteristics. The intermediate layer comprises a resin as the main component. The photoconductive layer is provided on the intermediate layer by coating method using a solvent, so that it is desirable that the resin for use in the intermediate layer have high resistance against general-purpose organic solvents.

Preferable examples of the resin for use in the intermediate layer include water-soluble resins such as polyvinyl alcohol, casein and sodium polyacrylate; alcohol-soluble resins such as copolymer nylon and methoxymethylated nylon; and hardening resins with three-dimensional network such as polyurethane, melamine resin, phenolic resin, alkyd-melamine resin and epoxy resin.

The intermediate layer may further comprise finely-divided particles of metallic oxides such as titanium oxide, silica, alumina, zirconium oxide, tin oxide and indium oxide in order to prevent the occurrence of Moiré and reduce the residual potential.

Similar to the previously mentioned photoconductive layer, the intermediate layer can be provided on the electroconductive support by coating method, using an appropriate solvent.

Further, the intermediate layer for use in the present invention may be prepared using a coupling agent such as a silane coupling agent, titanium coupling agent or chromium coupling agent. Furthermore, to prepare the intermediate layer, $Al_2O_3$ may be deposited on the electroconductive support by anodizing process, or an organic material such as poly-para-xylylene (parylene), or an inorganic material such as $SiO_2$, $SnO_2$, $TiO_2$, ITO or $CeO_2$ may be deposited on the electroconductive support by vacuum thin-film forming method.

It is proper that the thickness of the intermediate layer be 5 μm or less.

In order to improve the mechanical durability in terms of the friction resistance, the electrophotographic photoconductor according to the present invention may further comprise a protective layer which is provided on the photoconductive layer.

The protective layer for use in the present invention comprises a resin. Examples of such a resin for use in the protective layer include ABS resin, ACS resin, copolymer of olefin and vinyl monomer, chlorinated polyether, allyl resin, phenolic resin, polyacetal, polyamide, polyamideimide, polyacrylate, polyallyl sulfone, polybutylene, polybutylene terephthalate, polycarbonate, polyether sulfone, polyethylene, polyethylene terephthalate, polyimide, acrylic resin, polymethylpentene, polypropylene, polyphenylene oxide, polysulfone, polystyrene, AS resin, butadiene-styrene copolymer, polyurethane, polyvinyl chloride, polyvinylidene chloride and epoxy resin.

The protective layer may further comprise a fluorine-containing resin such as polytetrafluoroethylene, and a silicone resin to improve the abrasion resistance. In addition, inorganic materials such as titanium oxide, tin oxide and potassium titanate may be dispersed in the above-mentioned resins.

The protective layer may be provided on the photoconductive layer by the conventional coating method. The thickness of the protective layer is preferably in the range of about 0.1 to 10 μm. Furthermore, a vacuum-deposited thin film of a-C or a-SiC may be used as the protective layer in the present invention.

The charge transport material for use in the photoconductive layer include a positive hole transport material and an electron transport material.

There can be employed any conventional positive hole transport materials, for example, poly-N-carbazole and derivatives thereof, poly-γ-carbazolyl ethylglutamate and derivatives thereof, a condensation product of pyrene and formaldehyde and derivatives thereof, polyvinyl pyrene, polyvinyl phenanthrene, oxazole derivatives, imidazole derivatives, triphenylamine derivatives, and the compounds to be described later.

Specific examples of the positive hole transport material for use in the present invention are as follows:

(1) [Positive hole transport material in Japanese Laid-Open Patent Applications Nos. 55-154955 and 55-156954]

(1)

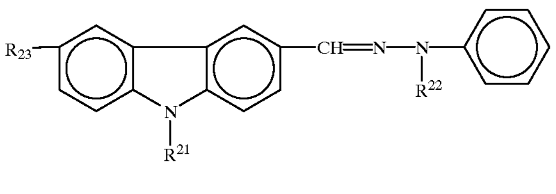

wherein $R^{21}$ is methyl group, ethyl group, 2-hydroxyethyl group or 2-chloroethyl group; $R^{22}$ is methyl group, ethyl group, benzyl group or phenyl group; and $R^{23}$ is a hydrogen atom, a chlorine atom, a bromine atom, an alkyl group having 1 to 4 carbon atoms, an alkoxyl group having 1 to 4 carbon atoms, a dialkylamino group or nitro group.

Examples of the above compound of formula (1) are 9-ethylcarbazole-3-aldehyde-1-methyl-1-phenylhydrazone, 9-ethylcarbazole-3-aldehyde-1-benzyl-1-phenylhydrazone, and 9-ethylcarbazole-3-aldehyde-1,1-diphenylhydrazone.

(2) [Positive hole transport material in Japanese Laid-Open Patent Application No. 55-52063]

(2)

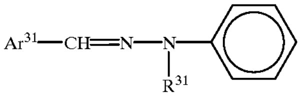

wherein $Ar^{31}$ is a naphthalene ring, anthracene ring or styryl ring, each of which may have a substituent, a pyridine ring, furan ring, or thiophene ring; and $R^{31}$ is an alkyl group or benzyl group.

Examples of the above compound of formula (2) are 4-diethylaminostyryl-β-aldehyde-1-methyl-1-phenylhydrazone, and 4-methoxynaphthalene-1-aldehyde-1-benzyl-1-phenylhydrazone.

(3) [Positive hole transport material in Japanese Laid-Open Patent Application No. 56-81850]

(3)

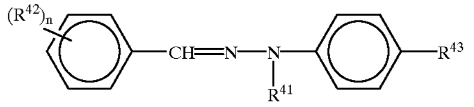

wherein $R^{41}$ is an alkyl group, benzyl group, phenyl group or naphthyl group; $R^{42}$ is a hydrogen atom, an alkyl group having 1 to 3 carbon atoms, an alkoxyl group having 1 to 3 carbon atoms, a dialkylamino group, a diaralkylamino group or a diarylamino group; n is an integer of 1 to 4, and when n is 2 or more, $R^{42}$ may be the same or different; and $R^{43}$ is a hydrogen atom or methoxy group.

Examples of the above compound of formula (3) are 4-methoxybenzaldehyde-1-methyl-1-phenylhydrazone, 2,4-dimethoxybenzaldehyde-1-benzyl-1-phenylhydrazone, 4-diethylaminobenzaldehyde-1,1-diphenylhydrazone, 4-methoxybenzaldehyde-1-(4-methoxy)phenylhydrazone, 4-diphenylaminobenzaldehyde-1-benzyl-1-phenylhydrazone, and 4-dibenzylaminobenzaldehyde-1,1-diphenylhydrazone (4) [Positive hole transport material in Japanese Laid-Open Patent Application No. 51-109831]

(4)

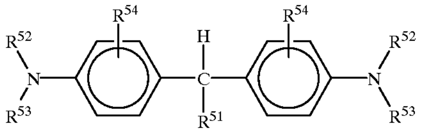

wherein $R^{51}$ is an alkyl group having 1 to 11 carbon atoms, a substituted or unsubstituted phenyl group, or a heterocyclic group; $R^{52}$ and $R^{53}$ are each independently a hydrogen atom, an alkyl group having 1 to 4 carbon atoms, a hydroxyalkyl group, chloroalkyl group, or a substituted or unsubstituted aralkyl group, and $R^{52}$ and $R^{53}$ may form a nitrogen-containing heterocyclic ring in combination; and $R^{54}$, which may be the same or different, each is a hydrogen atom, an alkyl group having 1 to 4 carbon atoms, an alkoxyl group, or a halogen atom.

Examples of the above compound of formula (4) are 1,1-bis(4-dibenzylaminophenyl)propane, tris(4-diethylaminophenyl)methane, 1,1-bis(4-dibenzylaminophenyl)propane, and 2,2-dimethyl-4,4-bis(diethylamino)triphenylmethane.

(5) [Positive hole transport material in Japanese Laid-Open Patent Application No. 51-94829]

(5)

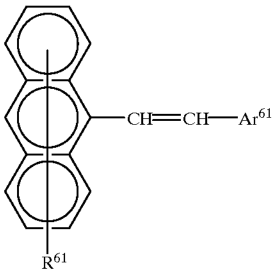

wherein $R^{61}$ is a hydrogen atom or a halogen atom; and $Ar^{61}$ is a substituted or unsubstituted phenyl group, naphthyl group, anthryl group, or carbazolyl group.

Examples of the above compound of formula (5) are 9-(4-diethylaminostyryl)anthracene, and 9-bromo-10-(4-diethylaminostyryl)anthracene.

(6) [Positive hole transport material in Japanese Laid-Open Patent Application No. 52-128373]

(6)

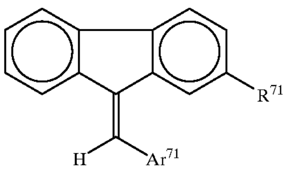

wherein $R^{71}$ is a hydrogen atom, a halogen atom, cyano group, an alkoxyl group having 1 to 4 carbon atoms, or an alkyl group having 1 to 4 carbon atoms; and $Ar^{71}$ is

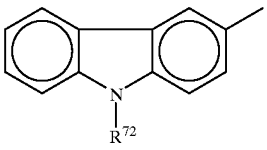

, or

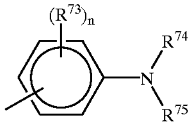

in which $R^{72}$ is an alkyl group having 1 to 4 carbon atoms; $R^{73}$ is a hydrogen atom, a halogen atom, an alkyl group having 1 to 4 carbon atoms, an alkoxyl group having 1 to 4 carbon atoms, or a dialkylamino group; n is an integer of 1 or 2, and when n is 2, $R^{73}$ may be the same or different; and $R^{74}$ and $R^{75}$ are each a hydrogen atom, a substituted or unsubstituted alkyl group having 1 to 4 carbon atoms, or a substituted or unsubstituted benzyl group.

Examples of the above compound of formula (6) are 9-(4-dimethylaminobenzylidene)fluorene, and 3-(9-fluorenylidene)-9-ethylcarbazole.

(7) [Positive hole transport material in Japanese Laid-Open Patent Application No. 56-29245]

(7)

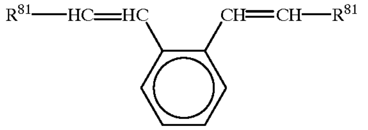

wherein $R^{81}$ is carbazolyl group, pyridyl group, thienyl group, indolyl group, furyl group, a substituted or unsubstituted phenyl group, a substituted or unsubstituted styryl group, a substituted or unsubstituted naphthyl group, or a substituted or unsubstituted anthryl group, each of which may have a substituent selected from the group consisting of a dialkylamino group, an alkyl group, an alkoxyl group, carboxyl group and an ester group thereof, a halogen atom, cyano group, an aralkylamino group, an N-alkyl-N-aralkylamino group, amino group, nitro group and acetylamino group.

Examples of the above compound of formula (7) are 1,2-bis(4-diethylaminostyryl)benzene, and 1,2-bis(2,4-dimethoxystyryl)benzene.

(8) [Positive hole transport material in Japanese Laid-Open Patent Application No. 58-58552]

(8)

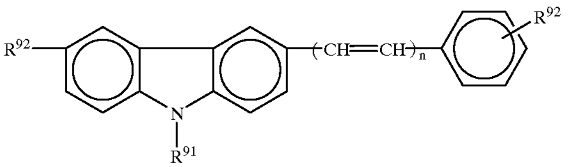

wherein $R^{91}$ is a lower alkyl group, a substituted or unsubstituted phenyl group, or benzyl group; $R^{92}$ is a hydrogen atom, a lower alkyl group, a lower alkoxyl group, a halogen atom, nitro group, or an amino group which may have as a substituent a lower alkyl group or benzyl group; and n is an integer of 1 or 2.

Examples of the above compound of formula (8) are 3-styryl-9-ethylcarbazole, and 3-(4-methoxystyryl)-9-ethylcarbazole.

(9) [Positive hole transport material in Japanese Laid-Open Patent Application No. 57-73075]

(9)

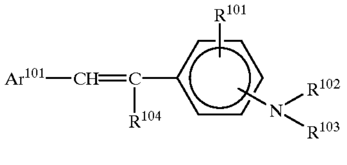

wherein $R^{101}$ is a hydrogen atom, an alkyl group, an alkoxyl group, or a halogen atom; $R^{102}$ and $R^{103}$ are each an alkyl group, a substituted or unsubstituted aralkyl group, or a substituted or unsubstituted aryl group; $R^{104}$ is a hydrogen atom, a lower alkyl group, or a substituted or unsubstituted phenyl group; and $Ar^{101}$ is a substituted or unsubstituted phenyl group, or a substituted or unsubstituted naphthyl group.

Examples of the above compound of formula (9) are 4-diphenylaminostilbene, 4-dibenzylaminostilbene, 4-ditolylaminostilbene, 1-(4-diphenylaminostyryl) naphthalene, and 1-(4-diethylaminostyryl)naphthalene.

(10) [Positive hole transport material in Japanese Laid-Open Patent Application No. 58-198043]

(10)

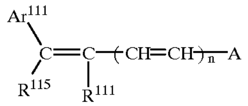

wherein n is an integer of 0 or 1, and when n=0, A and $R^{111}$ may form a ring in combination; $R^{111}$ is a hydrogen atom, an alkyl group, or a substituted or unsubstituted phenyl group; $Ar^{111}$ is a substituted or unsubstituted aryl group; $R^{115}$ is a substituted or unsubstituted alkyl group, or a substituted or unsubstituted aryl group; and A is 9-anthryl group, a substituted or unsubstituted carbazolyl group, or

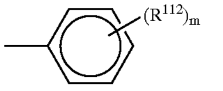

or

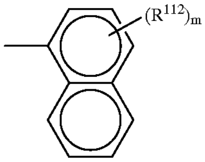

in which m is an integer of 0 to 3, and when m is 2 or more, $R^{112}$ may be the same or different; and $R^{112}$ is a hydrogen atom, an alkyl group, an alkoxyl group, a halogen atom, or

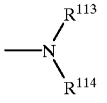

in which $R^{113}$ and $R^{114}$ are each independently an alkyl group, a substituted or unsubstituted aralkyl group, or a substituted or unsubstituted aryl group, and $R^{113}$ and $R^{114}$ may form a ring in combination.

Examples of the above compound of formula (10) are 4'-diphenylamino-α-phenylstilbene, and 4'-bis(methylphenyl)amino-α-phenylstilbene.

(11) [Positive hole transport material in Japanese Laid-Open Patent Application No. 49-105537]

(11)

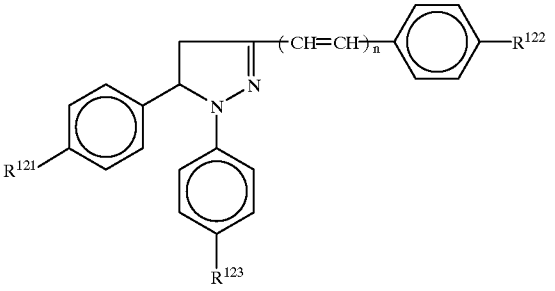

wherein $R^{121}$, $R^{122}$ and $R^{123}$ are each a hydrogen atom, a lower alkyl group, a lower alkoxyl group, a dialkylamino group, or a halogen atom; and n is an integer of 0 or 1.

Examples of the above compound of formula (11) include 1-phenyl-3-(4-diethylaminostyryl)-5-(4-diethylaminophenyl)pyrazoline.

(12) [Positive hole transport material in Japanese Laid-Open Patent Application No. 52-139066]

(12)

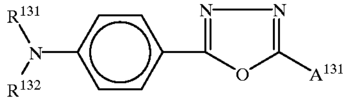

wherein $R^{131}$ and $R^{132}$ are each a substituted or unsubstituted alkyl group, or s substituted or unsubstituted aryl group; and $A^{131}$ is a substituted amino group, a substituted or unsubstituted aryl group, or an allyl group.

Examples of the above compound of formula (12) are 2,5-bis(4-diethylaminophenyl)-1,3,4-oxadiazole, 2-N,N-diphenylamino-5-(4-diethylaminophenyl)-1,3,4-oxadiazole, and 2-(4-dimethylaminophenyl)-5-(4-diethylaminophenyl)-1,3,4-oxadiazole.

(13) [Positive hole transport material in Japanese Laid-Open Patent Application No. 52-139065]

(13)

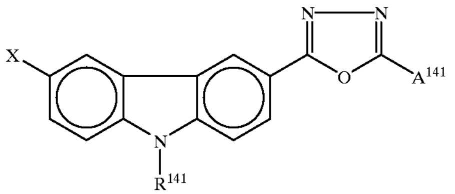

wherein X is a hydrogen atom, a lower alkyl group, or a halogen atom; $R^{141}$ is a substituted or unsubstituted alkyl group, or a substituted or unsubstituted aryl group; and $A^{141}$ is a substituted amino group, or a substituted or unsubstituted aryl group.

Examples of the above compound of formula (13) are 2-N,N-diphenylamino-5-(N-ethylcarbazol-3-yl)-1,3,4-oxadiazole, and 2-(4-diethylaminophenyl)-5-(N-ethylcarbazol-3-yl)-1,3,4-oxadiazole.

(14) [Positive hole transport material in Japanese Laid-Open Patent Application No. 58-32372]

(14)

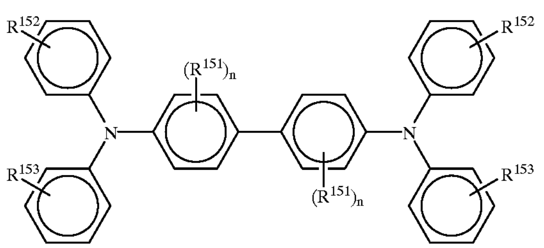

wherein $R^{151}$ is a lower alkyl group, a lower alkoxyl group, or a halogen atom; n is an integer of 0 to 4; and $R^{152}$ and $R^{153}$ are each independently a hydrogen atom, a lower alkyl group, a lower alkoxyl group, or a halogen atom.

Examples of the benzidine compound of formula (14) are N,N-diphenyl-N,N-bis(3-methylphenyl)-[1,1-biphenyl]-4,4-diamine, and 3,3-dimethyl-N,N,N,N-tetrakis(4-methylphenyl)-[1,1-biphenyl]-4,4-diamine.

(15) [Positive hole transport material in Japanese Laid-Open Patent Application No. 2-178669]

(15)

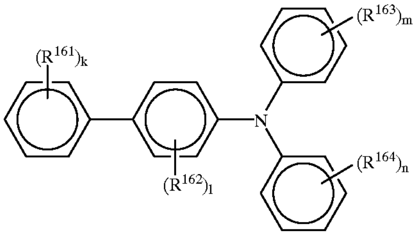

wherein $R^{161}$, $R^{163}$ and $R^{164}$ are each a hydrogen atom, amino group, an alkoxyl group, a thioalkoxyl group, an aryloxy group, methylenedioxy group, a substituted or unsubstituted alkyl group, a halogen atom, or a substituted or unsubstituted aryl group; $R^{162}$ is a hydrogen atom, an alkoxyl group, a substituted or unsubstituted alkyl group, or a halogen atom, provided that $R^{161}$, $R^{162}$, $R^{163}$ and $R^{164}$ are not hydrogen atoms at the same time; and k, l, m and n are each an integer of 1 to 4, and when each is an integer of 2, 3 or 4, $R^{161}$, $R^{162}$, $R^{163}$ and $R^{164}$ may be independently the same or different.

Examples of the biphenylamine compound of formula (15) are 4-methoxy-N,N-diphenyl-[1,1-biphenyl]-4-amine, 4-methyl-N,N-bis(4-methylphenyl)-[1,1-biphenyl]-4-amine, and 4-methoxy-N,N-bis(4-methylphenyl)-[1,1-biphenyl]-4-amine.

(16) [Positive hole transport material in Japanese Laid-Open Patent Application No. 3-285960]

(16)

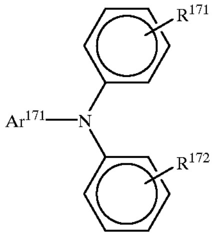

wherein $Ar^{171}$ is a condensed polycyclic hydrocarbon group having 18 or less carbon atoms; and $R^{171}$ and $R^{172}$ are each independently a hydrogen atom, a halogen atom, a substituted or unsubstituted alkyl group, an alkoxyl group, or a substituted or unsubstituted phenyl group.

Examples of the triarylamine compound of formula (16) are 1-diphenylaminopyrene, and 1-di(p-tolylamino)pyrene.

(17) [Positive hole transport material in Japanese Laid-Open Patent Application No. 62-98394]

$$A^{181}—CH{=}CH—Ar^{181}—CH{=}CH—A^{181} \quad (17)$$

wherein $Ar^{181}$ is a substituted or unsubstituted aromatic hydrocarbon group; and $A^{181}$ is

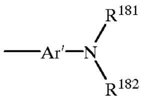

in which Ar' is a substituted or unsubstituted aromatic hydrocarbon group; and $R^{181}$ and $R^{182}$ are each a substituted or unsubstituted alkyl group, or a substituted or unsubstituted aryl group.

Examples of the diolefin aromatic compound of formula (17) are 1,4-bis(4-diphenylaminostyryl)benzene, and 1,4-bis [4-di(p-tolyl)aminostyryl]benzene.

(18) [Positive hole transport material in Japanese Laid-Open Patent Application No. 4-230764]

(18)

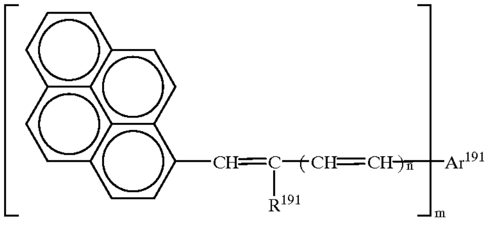

wherein $Ar^{191}$ is a substituted or unsubstituted aromatic hydrocarbon group; $R^{191}$ is a hydrogen atom, a substituted or unsubstituted alkyl group, or a substituted or unsubstituted aryl group; and n is an integer of 0 or 1, and m is an integer of 1 or 2, and when n=0 and m=1, $Ar^{191}$ and $R^{191}$ may form a ring in combination.

Examples of the styrylpyrene compound of formula (18) are 1-(4-diphenylaminostyryl)pyrene, and 1-[4-di(p-tolyl) aminostyryl]pyrene.

Examples of the electron transport material for use in the present invention are chloroanil, bromoanil, tetracyanoethylene, tetracyanoquinodimethane, 2,4,7-trinitro-9-fluorenone, 2,4,5,7-tetranitro-9-fluorenone, 2,4,5,7-tetranitroxanthone, 2,4,8-trinitrothioxanthone, 2,6,8-trinitro-indeno4H-indeno[1,2-b]thiophen-4-one, and 1,3,7-trinitrodibenzothiophene-5,5-dioxide.

In particular, the following charge transport materials of formulas (19) to (21) are preferably employed.

(19)

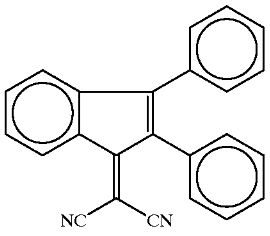

-continued (20)

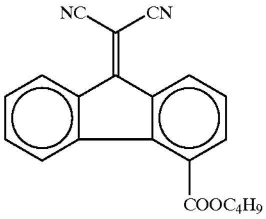

(21)

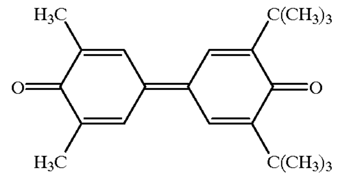

These charge transport materials may be used alone or in combination.

The method of producing the previously mentioned bisazo compound of formula (I) according to the present invention will now be explained in detail.

The bisazo compound of formula (I) can be prepared by allowing a bis(diazonium salt) compound of formula (III) to react with a corresponding coupler.

The above-mentioned bis(diazonium salt) compound of formula (III) can be prepared by reducing 1,4-bis[4-(4-nitrophenyl)-1,3-butadienyl]benzene of formula (V) to prepare 1,4-bis[4-(4-aminophenyl)-1,3-butadienyl]benzene of formula (VI), and subjecting 1,4-bis[4-(4-aminophenyl)-1,3-butadienyl]benzene thus prepared to diazotization:

(V)

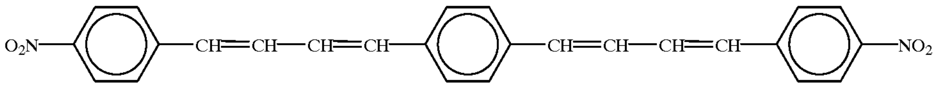

(VI)

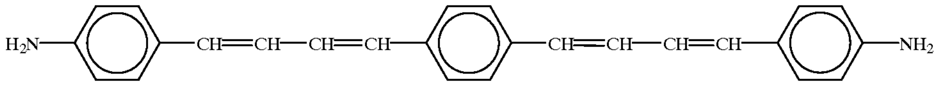

Namely, the previously mentioned bis(diazonium salt) compound of formula (III), 1,4-bis[4-(4-aminophenyl)-1,3-butadienyl]benzene of formula (VI), and 1,4-bis[4-(4-nitrophenyl)-1,3-butadienyl]benzene of formula (V), which are novel compounds, are useful as the raw materials for the preparation of the bisazo compound of formula (I) capable of serving as the organic photoconductive material for use in the electrophotographic photoconductor according to the present invention.

The method of producing 1,4-bis[4-(4-nitrophenyl)-1,3-butadienyl]benzene of formula (V) comprises the step of allowing a bis(phosphonium salt) compound of formula (VII) to react with 4-nitrocinnamaldehyde:

(VII)

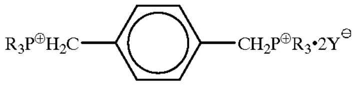

wherein R is phenyl group or an alkyl group; and $Y^{\ominus}$ is a halogen ion.

Alternatively, 1,4-bis[4-(4-nitrophenyl)-1,3-butadienyl] benzene of formula (V) can be prepared by allowing a phosphonate of formula (VIII) to react with terephthalaldehyde:

(VIII)

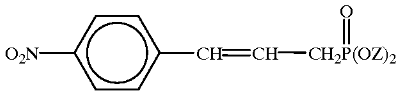

wherein Z is a lower alkyl group.

Specific examples of the alkyl group represented by R in formula (VII) and Z in formula (VIII) are methyl group, ethyl group, propyl group and butyl group.

In the bis(phosphonium salt) compound of formula (VII), there can be employed chlorine ion, bromine ion and iodine ion as the halogen ion represented by $Y^{\ominus}$ in formula (VII).

The reaction between the bis(phosphonium salt) compound of formula (VII) and 4-nitrocinnamaldehyde, or the reaction between the phosphonate compound of formula (VIII) and terephthalaldehyde is carried out in the presence of a basic catalyst at temperature in the range from room temperature to about 100° C.

In the above-mentioned reaction, sodium hydroxide, potassium hydroxide, sodium amide, sodium hydride, phenyl lithium, n-butyl lithium, lithium methoxide, sodium methoxide and potassium-t-butoxide are preferably used as the basic catalysts.

Examples of the reaction solvent used in the above-mentioned reaction are methanol, ethanol, isopropanol, butanol, 2-methoxyethanol, 1,2-dimethoxyethane, bis(2-methoxyethyl)ether, diethyl ether, dioxane, tetrahydrofuran, toluene, xylene, dimethyl sulfoxide, N,N-dimethylformamide, N-methylpyrrolidone and 1,3-dimethyl-2-imidazolidinone.

The reaction temperature in the reaction may be determined within a wide range from room temperature to about 100° C. depending on (1) the stability of the employed solvent with respect to the employed basic catalyst, (2) the reactivity of the condensed components, and (3) the reactivity of the employed basic catalyst as a condensation agent in the solvent. Further, it is preferable to carry out the reaction in an atmosphere of an inert gas because oxidation of the phosphonium salt compound can be inhibited in the course of the reaction.

In the thus obtained dinitro compound, part of a moiety of olefin has a cis-form. By heating the crude product as it is, or after purification, in an aromatic hydrocarbon solvent such as toluene or xylene together with a catalytic amount of iodine, all the olefin moiety can become trans-form.

The thus prepared 1,4-bis[4-(4-nitrophenyl)-1,3-butadienyl]benzene of formula (V) is reduced in such a manner that 1,4-bis[4-(4-nitrophenyl)-1,3-butadienyl] benzene is heated to temperature in the range of 70 to 120° C. using a reducing agent such as iron-hydrochloric acid or stannous chloride-hydrochloric acid. Thus, 1,4-bis[4-(4-aminophenyl)-1,3-butadienyl]benzene of formula (VI) can be obtained. This reaction is terminated in about 0.5 to 3 hours. When the reducing agent of iron-hydrochloric acid is employed, it is preferable to carry out the reaction in an organic solvent such as N,N-dimethylformamide.

According to the present invention, 1,4-bis[4-(4-aminophenyl)-1,3-butadienyl]benzene of formula (VI) is subjected to diazotization to prepare the bis(diazonium salt) compound of formula (III). Such diazotization is carried out in such a manner that 1,4-bis[4-(4-aminophenyl)-1,3-butadienyl]benzene of formula (VI) is dispersed in an inorganic acid such as hydrochloric acid or sulfuric acid to prepare a dispersion, and sodium nitrite is added to the dispersion at temperature in the range of −10 to 20° C. This reaction is terminated in about 0.5 to 3 hours, thereby obtaining a bis(diazonium salt) compound of formula (III).

Further, the bis(diazonium salt) compound of formula (III) can be isolated as a salt from the reaction mixture by adding an aqueous solution of borofluoric acid or sodium borofluoride to the above-mentioned reaction mixture.

Of the bisazo compound of formula (I), the following bisazo compound represented by formula (II) is preferable in the present invention:

(II)

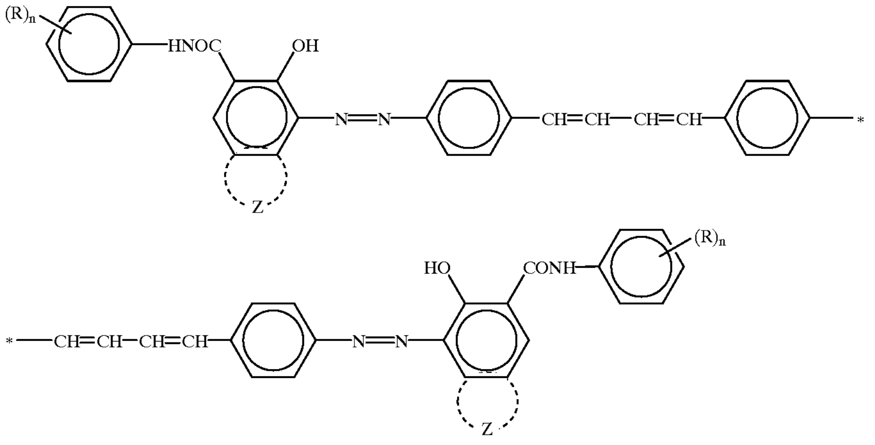

wherein Z is a benzene ring, a naphthalene ring or a carbazole ring, each of which may have a substituent; R is independently a hydrogen atom, a halogen atom, a lower alkyl group, a lower alkoxyl group or nitro group; n is an integer of 1, 2 or 3.

The bisazo compound of formula (II) can be prepared by allowing the previously mentioned bis(diazonium salt) compound of formula (III) to react with a coupler of formula (IV):

(III)

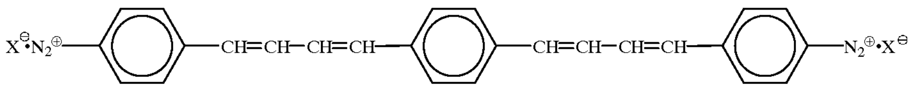

wherein X is an anionic functional group; and (IV)

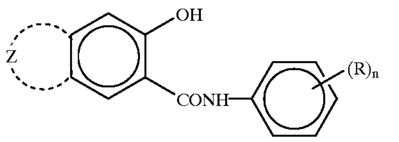

wherein Z is a benzene ring, a naphthalene ring or a carbazole ring, each of which may have a substituent; R is independently a hydrogen atom, a halogen atom, a lower alkyl group, a lower alkoxyl group or nitro group; and n is an integer of 1, 2 or 3.

Specific examples of the halogen atom represented by R in formula (II) or (IV) are fluorine atom, chlorine atom, bromine atom and iodine atom.

Specific examples of the lower alkyl group represented by R in formula (II) or (IV) are methyl group, ethyl group, propyl group and butyl group.

Specific examples of the lower alkoxyl group represented by R in formula (II) or (IV) are methoxy group, ethoxy group, propoxy group and butoxy group.

In formula (II) or (IV), Z represents benzene ring, naphthalene ring or carbazole ring, each of which may have a substituent. As the substituent, there can be employed the same halogen atom, lower alkyl group, lower alkoxyl group, and nitro group as mentioned in the explanation of R.

The bisazo compound of formula (II) can be prepared by the following method. The bis(diazonium salt) compound of formula (III) and the coupler of formula (IV) are dissolved in an organic solvent such as N,N-dimethylformamide (DMF) or dimethyl sulfoxide to prepare a solution, and an alkaline aqueous solution such as an aqueous solution of sodium acetate is added dropwise to the above prepared solution at temperature in the range of about −10 to 40° C. to carry out the coupling reaction. This coupling reaction is terminated in about 5 minutes to 3 hours. After completion of the coupling reaction, separating crystals are collected by filtration, and purified by washing the crystals with water and/or an organic solvent and carrying out recrystallization. Thus, a desired bisazo compound of formula (II) can be obtained.

The bisazo compound of formula (II) can also be prepared by allowing the reaction mixture prepared for diazotization of 1,4-bis[4-(4-aminophenyl)-1,3-butadienyl]benzene to directly react with the coupler of formula (IV).

The bisazo compound of formula (II) can serve as the organic photoconductive material, in particular, the charge generation material in the electrophotographic photoconductor.

For example, a single-layered photoconductor can be fabricated by overlaying on an electroconductive support a photoconductive layer comprising the bisazo compound of formula (II) and a binder resin, optionally in combination with a sensitizing agent.

The above-mentioned single-layered photoconductive layer may further comprise a charge transport material.

Alternatively, a layered photoconductor can be fabricated by providing a charge generation layer comprising the bisazo compound of formula (II) as the main component on an electroconductive support, and overlaying a charge transport layer comprising a charge transport material and a binder resin on the charge generation layer.

In the above-mentioned layered photoconductor, the overlaying order of the charge generation layer and the charge transport layer may be reversed.

The bisazo compound according to the present invention is useful as the photoconductive material for use in the electrophotographic photoconductor, and in addition, as the electronic device in the solar battery and the optical disk in the field of electronics.

Other features of this invention will become apparent in the course of the following description of exemplary embodiments, which are given for illustration of the invention and are not intended to be limiting thereof.

SYNTHESIS EXAMPLE 1

Synthesis of 1,4-bis[4-(4-nitrophenyl)-1,3-butadienyl]benzene

In a stream of argon gas, 59.14 g (0.075 mol) of p-xylylene-bis(triphenyl phosphonium bromide) was dissolved in 480 ml of dry methanol to prepare a solution. To this solution, 26.57 g (0.15 mol) of 4-nitrocinnamaldehyde was added, and the mixture thus obtained was stirred at room temperature for 15 minutes. Thereafter, 6.84 g (0.18 mol) of lithium methoxide was added to the above prepared reaction mixture at temperature in the range of 20 to 24° C. on a water bath over a period of 25 minutes. The resultant mixture was stirred at room temperature for 3 hours.

The reaction mixture was then neutralized with acetic acid. The separating crystals were collected by filtration, and successively washed with water and methanol, and dried with the application of heat under reduced pressure, whereby 30.12 g of the crude product in the form of orange powder was obtained in a 94.6% yield.

A mixture of the above obtained crude product and 3.00 g of iodine was put into 1.2 l of xylene, followed by stirring at 139 to 141° C. for 10 hours under the application of heat. Thereafter, the above mixture was cooled to room temperature and further stirred for 30 minutes, with 300 ml of a 10% aqueous solution of sodium sulfite being added thereto.

The resultant separating crystals were collected by filtration, and successively washed with water and methanol, and dried with the application of heat under reduced pressure, whereby 28.51 g of the product in the form of red powder was obtained in an 89.6% yield. This product was recrystallized from N,N-dimethylformamide (DMF), so that 1,4-bis[4-(4-nitrophenyl)-1,3-butadienyl]benzene was obtained as red crystals in the form of scales. The yield was 21.74 g (68.3%).

The melting point of the above compound was 318° C.

The results of the elemental analysis of the thus obtained compound were as follows:

| | % C | % H | % N |
|---|---|---|---|
| Calculated | 73.57 | 4.75 | 6.60 |
| Found | 73.69 | 4.63 | 6.59 |

FIG. 1 shows an IR spectrum of the above prepared 1,4-bis[4-(4-nitrophenyl)-1,3-butadienyl]benzene, taken by use of a KBr tablet.

The IR absorption of the above obtained compound indicates the appearance of the characteristic absorption peak based on the out-of-plane deformation vibration of the trans-olefin in the compound at 990 $cm^{-1}$, and the characteristic absorption peaks based on the stretching vibration of nitro group at 1510 $cm^{-1}$ and 1330 $cm^{-1}$.

SYNTHESIS EXAMPLE 2

Synthesis of 1,4-bis[4-(4-nitrophenyl)-1,3-butadienyl]benzene 18.85 g (63.0 mmol) of diethyl 4-nitrocinnamyl phosphate and 4.02 g (30.0 mmol) of terephthalaldehyde were dissolved in 130 ml of dry DMF to prepare a solution. To this DMF solution, a 28% methanol solution containing 13.89 g (72.0 mmol) of sodium methylate was added dropwise at temperature in the range of 22 to 27° C. on a water bath over a period of one hour and 25 minutes. The resultant mixture was stirred at room temperature for 3 hours.

The reaction mixture was then neutralized with acetic acid. With the addition of 130 ml of water to the reaction mixture, the separating crystals were collected by filtration, and successively washed with water and methanol, and dried with the application of heat under reduced pressure, whereby 9.60 g of the crude product in the form of orange powder was obtained in a 75.4% yield.

The above obtained crude product and 0.50 g of iodine were put into 300 ml of xylene, followed by stirring at 140 to 141° C. for 10 hours under the application of heat. Thereafter, the above mixture was cooled to room temperature and further stirred for 30 minutes, with 50 ml of a 10% aqueous solution of sodium sulfite being added thereto.

The resultant separating crystals were collected by filtration, and successively washed with water and methanol, and dried with the application of heat under reduced pressure, whereby 6.35 g of the product in the form of red powder was obtained in a 49.9% yield. This product was recrystallized from N,N-dimethylformamide (DMF), so that 1,4-bis[4-(4-nitrophenyl)-1,3-butadienyl]benzene was obtained as red crystals in the form of scales. The yield was 4.60 g (36.1%).

The melting point of the above compound was 320° C.

The results of the elemental analysis of the thus obtained compound were as follows:

| | % C | % H | % N |
|---|---|---|---|
| Calculated | 73.57 | 4.75 | 6.60 |
| Found | 73.55 | 4.66 | 6.78 |

Figure 2:
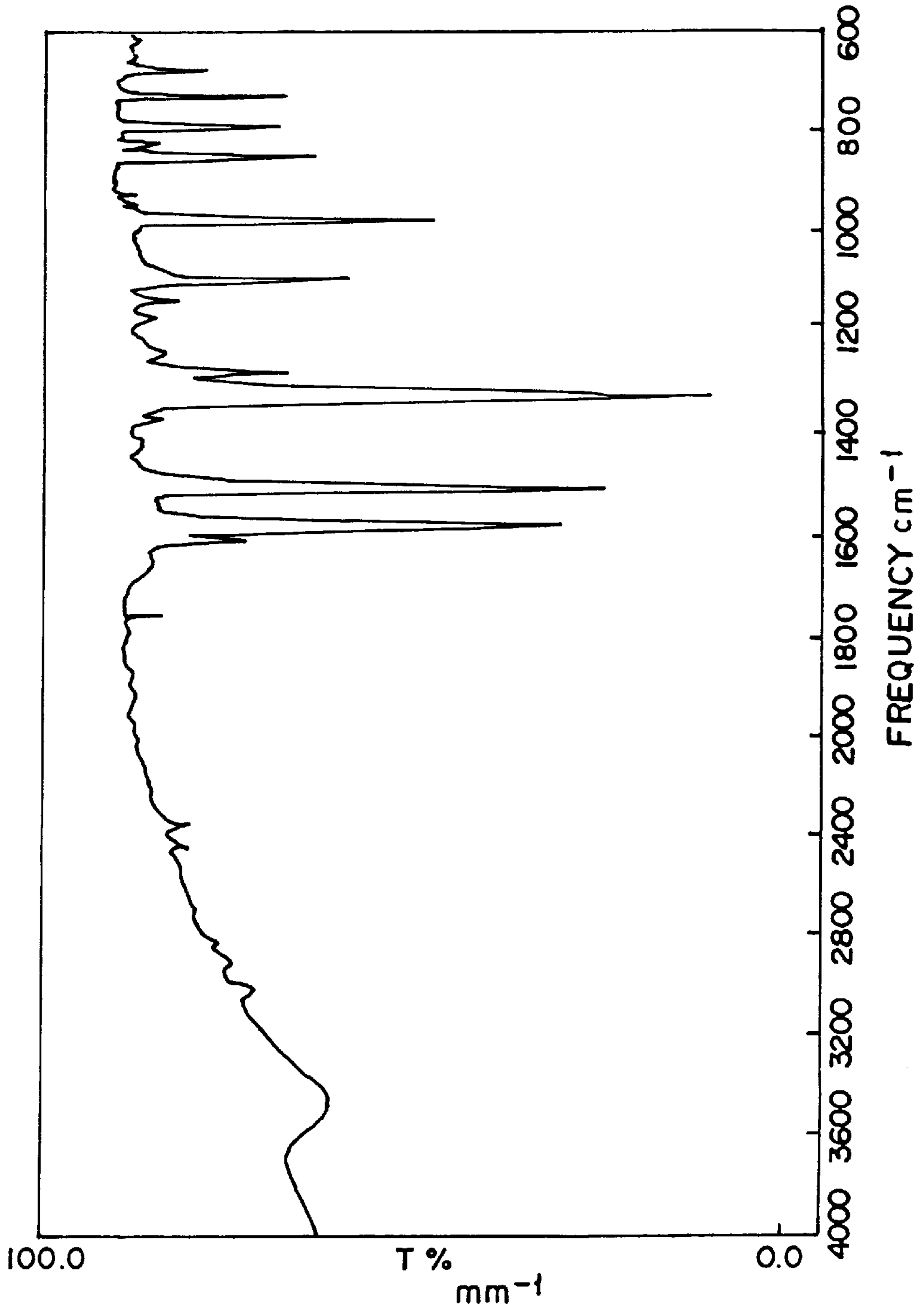
FIG. 2 is an IR spectrum of 1,4-bis[4-(4-nitrophenyl)-1,3-butadienyl]benzene according to the present invention, which is obtained in Synthesis Example 2.

FIG. 2 shows an IR spectrum of the above prepared 1,4-bis[4-(4-nitrophenyl)-1,3-butadienyl]benzene, taken by use of a KBr tablet.

The IR absorption of the above obtained compound indicates the appearance of the characteristic absorption peak based on the out-of-plane deformation vibration of the trans-olefin in the compound at 990 $cm^{-1}$, and the characteristic absorption peaks based on the stretching vibration of nitro group at 1515 $cm^{-1}$ and 1330 $cm^{-1}$.

SYNTHESIS EXAMPLE 3

Synthesis of 1,4-bis[4-(4-aminophenyl)-1,3-butadienyl]benzene 21.22 g of 1,4-bis[4-(4-nitrophenyl)-1,3-butadienyl]benzene was put into 800 ml of dimethylformamide (DMF). To this mixture, 33.51 g of iron powder and an aqueous solution of hydrochloric acid prepared by diluting 8.5 ml of concentrated hydrochloric acid with 28 ml of water were successively added with stirring, and the obtained mixture was further stirred at 95 to 102° C. for 4 hours. The resultant mixture was cooled to 90° C., and adjusted to pH 9 by the addition of a 40% aqueous solution of sodium hydroxide. Thereafter, the insoluble matter was removed from the mixture by filtration using Celite™. The filtrate was concentrated to about 400 ml under reduced pressure. With the addition of 20 ml of water, the concentrated filtrate was cooled to room temperature. The separating crystals were collected by filtration, and successively washed with water and methanol, and heated with the application of heat under reduced pressure, whereby 13.40 g of mud yellow crystals was obtained in a 73.5% yield.

The thus obtained crystals were recrystallized from a mixed solvent of 450 ml of N,N-dimethylformamide (DMF) and 50 ml of ethanol, so that 1,4-bis[4-(4-aminophenyl)-1,3-butadienyl]benzene was obtained as mud yellow crystals in the form of needles.

The exothermic peak temperature of the above compound was 309° C. when measured by DTA.

The results of the elemental analysis of the thus obtained compound were as follows:

| | % C | % H | % N |
|---|---|---|---|
| Calculated | 85.68 | 6.64 | 7.69 |
| Found | 85.22 | 6.61 | 7.82 |

Figure 3:
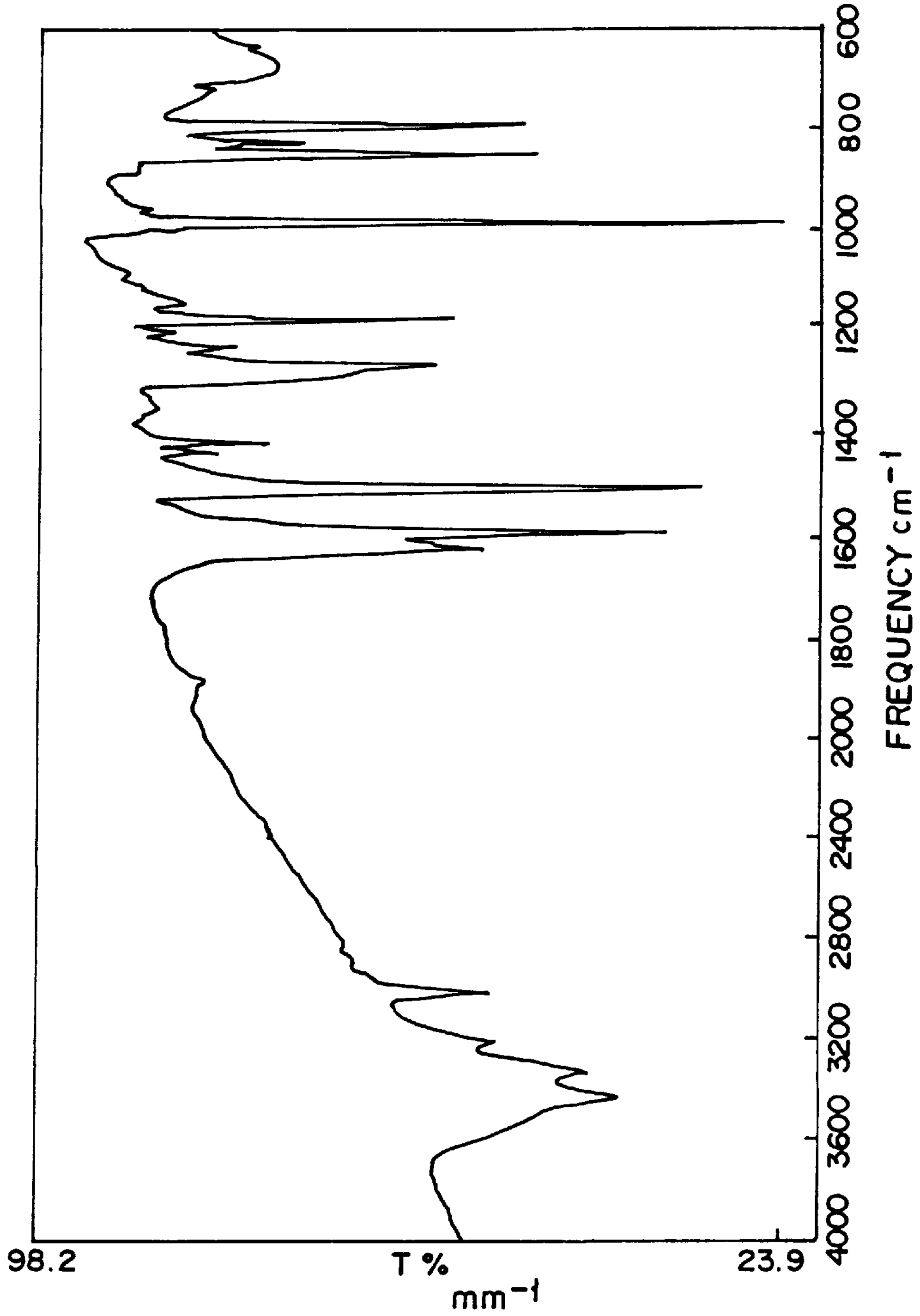
FIG. 3 is an IR spectrum of 1,4-bis[4-(4-aminophenyl)-1,3-butadienyl]benzene according to the present invention, which is obtained in Synthesis Example 3.

FIG. 3 shows an IR spectrum of the above prepared 1,4-bis[4-(4-aminophenyl)-1,3-butadienyl]benzene, taken by use of a KBr tablet.

The IR absorption of the above obtained compound indicates the appearance of the characteristic absorption peaks in the 3450 to 3200 $cm^{-1}$ region that are associated with stretching vibration of primary amine, and the characteristic absorption peak based on the out-of-plane deformation vibration of the trans-olefin in the compound at 990 $cm^{-1}$.

SYNTHESIS EXAMPLE 4

Synthesis of bis(diazonium salt) compound 3.64 g (10.0 mmol) of 1,4-bis[4-(4-aminophenyl)-1,3-butadienyl]benzene synthesized in Synthesis Example 3 was added to 100 ml of an aqueous solution of sulfuric acid (15 vol. %), and the mixture thus obtained was stirred at 60° C. for one hour. The mixture was then rapidly cooled to 2° C., and an aqueous solution prepared by dissolving 1.49 g (21.0 mmol) of sodium nitrite in 2.3 ml of water was added dropwise to the above-mentioned mixture over a period of 20 minutes at temperature in the range of 2 to 2.5° C. The resultant mixture was stirred at 1 to 2° C. for one hour.

Thereafter, the product thus generated was diluted with 300 ml of chilled water and a slight amount of insoluble matter was removed from the mixture by filtration using Celite™. With the addition of a 42% aqueous solution of borofluoric acid to the filtrate, the separating crystals were collected by filtration and, dried, whereby 2.95 g of a bis(diazonium salt) compound was obtained as dark red crystals in a 52.5% yield.

Figure 4:
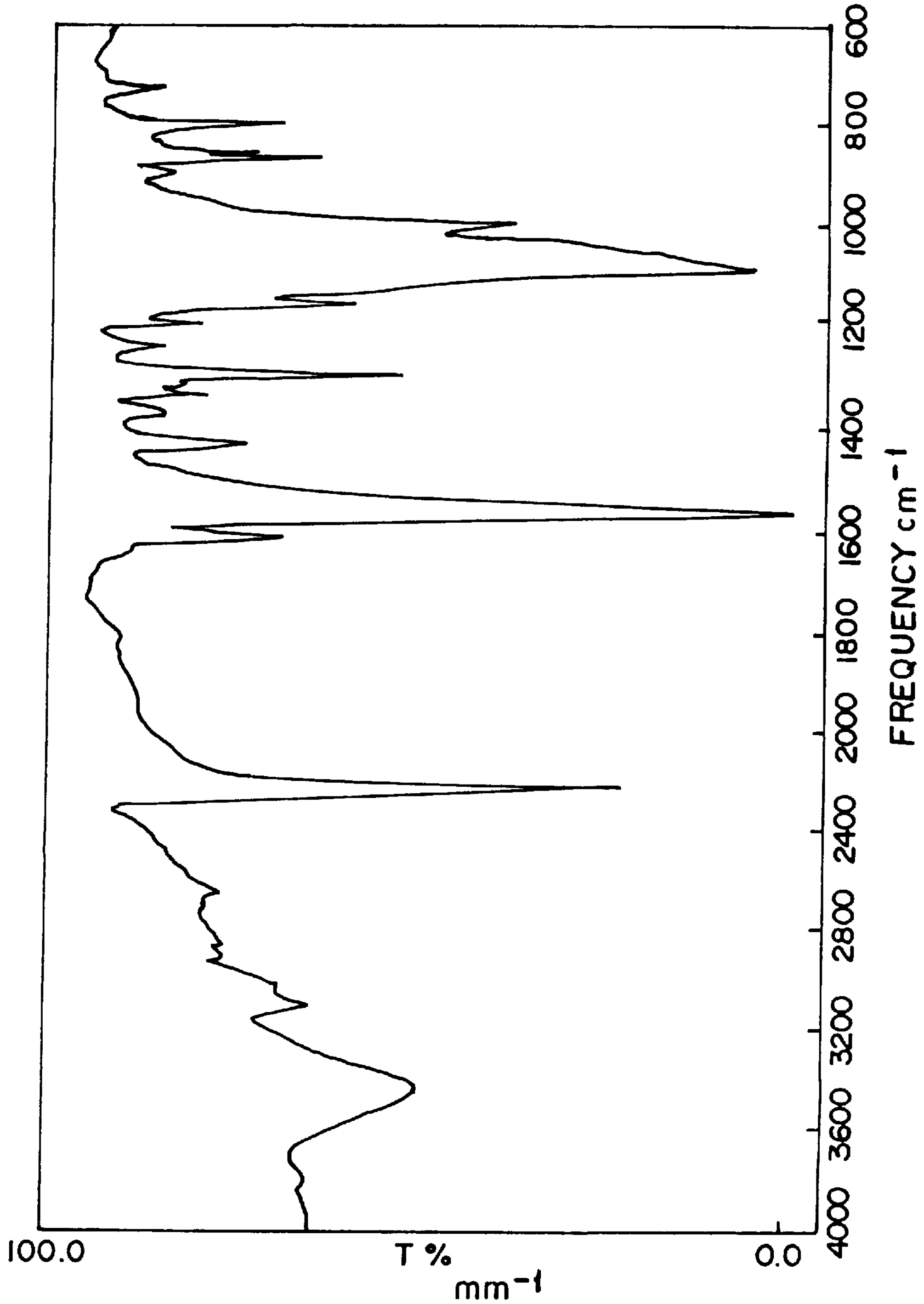
FIG. 4 is an IR spectrum of a bis(diazonium salt) compound according to the present invention, which is obtained in Synthesis Example 4.

FIG. 4 shows an IR spectrum of the above prepared bis(diazonium salt) compound, taken by use of a KBr tablet.

The IR absorption of the above obtained compound indicates the appearance of the characteristic absorption peak based on the stretching vibration of diazonium salt at 2230 $cm^{-1}$, and the characteristic absorption peak based on the out-of-plane deformation vibration of the trans-olefin in the compound at 1000 $cm^{-1}$.

EXAMPLE 1-1

Preparation of Bisazo Compound No. 1

0.527 g (2 mmol) of 3-hydroxy-2-naphthoic acid anilide (coupler No. 1 in TABLE 1) was dissolved in 100 ml of dimethylformamide (DMF) to prepare a solution. 0.562 g (1 mmol) of 1,4-bis[4-(phenyl-4-diazonium tetrafluoroborate)-1,3-butadienyl]benzene represented by the following formula (IX), that is, the bis(diazonium salt) compound synthesized in Synthesis Example 4, was added to the above-mentioned DMF solution, and thereafter, an aqueous solution prepared by dissolving 0.544 g (4 mmol) of sodium acetate·3 hydrate in 3 ml of water was added dropwise to the reaction mixture over a period of 20 minutes at room temperature.

(IX)

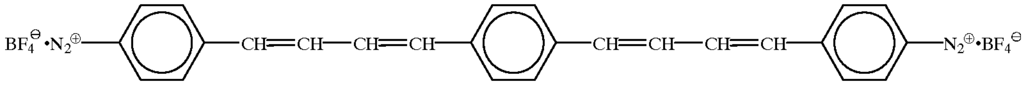

The above prepared reaction mixture was stirred at room temperature for 2 hours, thereby obtaining a bisazo compound. The thus obtained bisazo compound was filtered off, and successively washed with 100 ml of dimethylformamide three times, and washed with 100 ml of water twice. The compound was then dried with the application of heat thereto under reduced pressure, so that 0.640 g of a bisazo compound of formula (X) according to the present invention was obtained in a 70.1% yield.

(X)

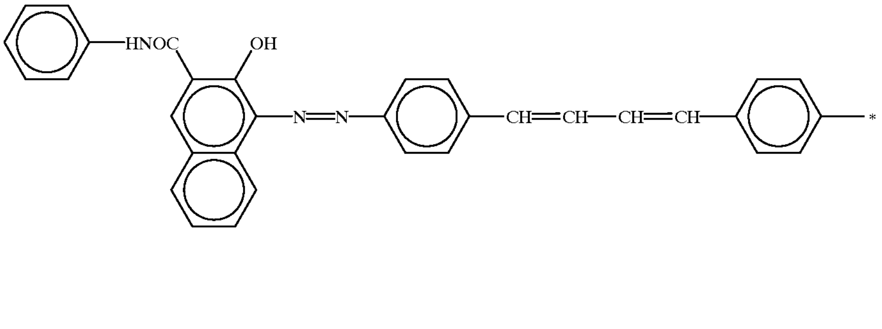

-continued

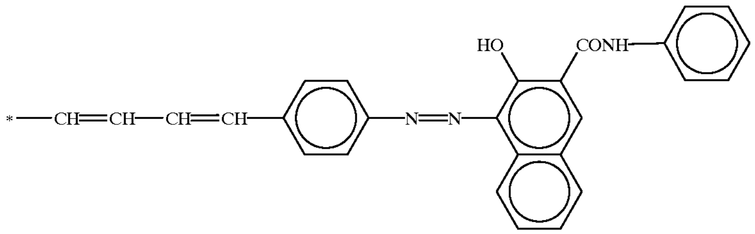

The results of the elemental analysis of the thus obtained bisazo compound were as follows:

| | % C | % H | % N |
|---|---|---|---|
| Calculated | 78.93 | 4.86 | 9.20 |
| Found | 79.17 | 4.75 | 9.18 |

The calculation is based on the formula for $C_{60}H_{44}N_6O_4$.

Figure 5:
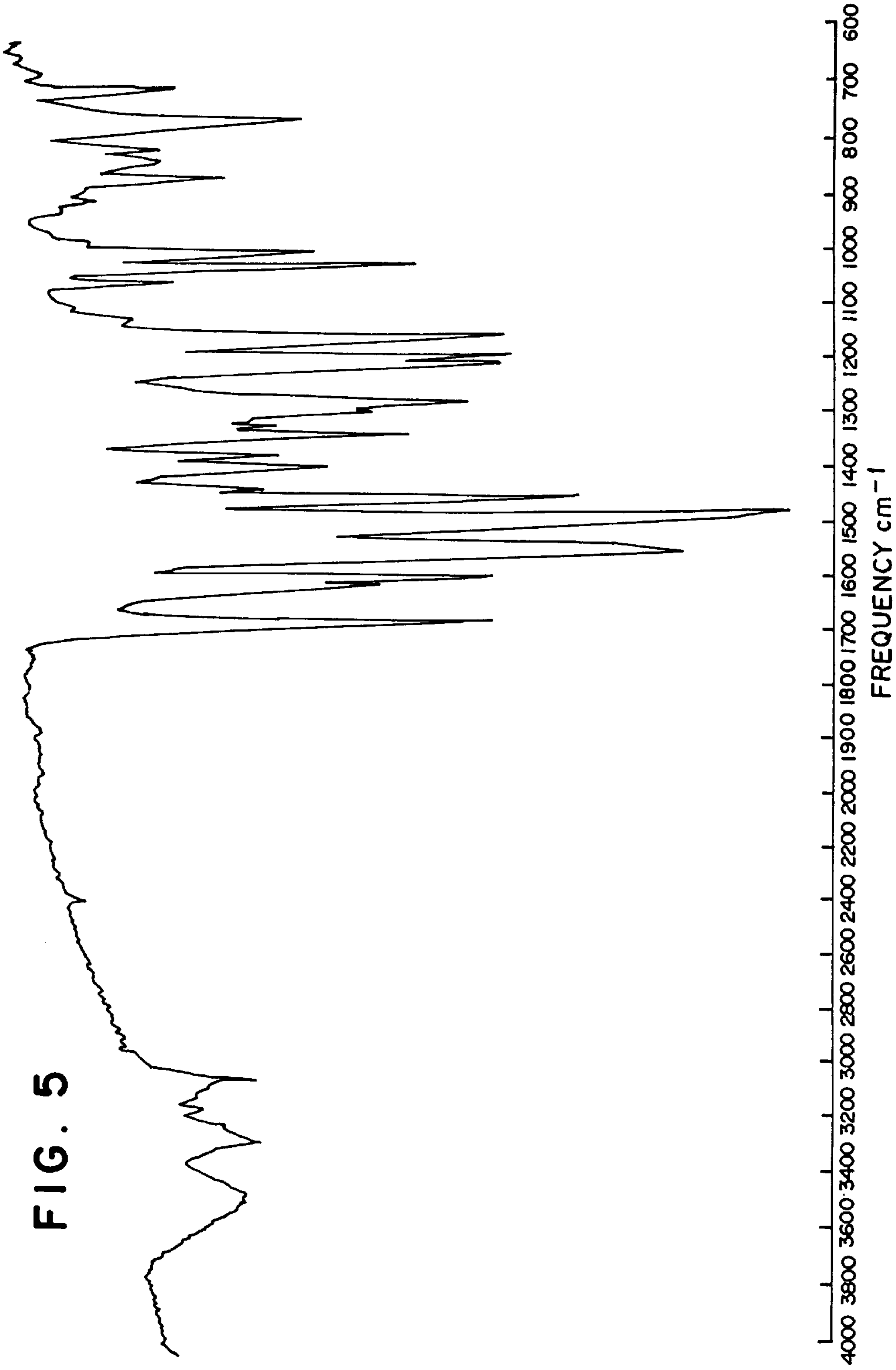
FIGS. 5 through 8 are IR spectra, using a KBr tablet, of bisazo compounds No. 1 to No. 4 according to the present invention, which are respectively obtained in Examples 1-1 to 1-4.

FIG. 5 shows an IR spectrum of the above prepared bisazo compound, taken by use of a KBr tablet.

The IR absorption of the above obtained bisazo compound indicates the appearance of the characteristic absorption peak based on C═O stretching vibration at 1675 $cm^{-1}$, and the characteristic absorption peak based on the C—H out-of-plane deformation vibration of the trans-olefin in the compound at 990 $cm^{-1}$.

Figure 6:
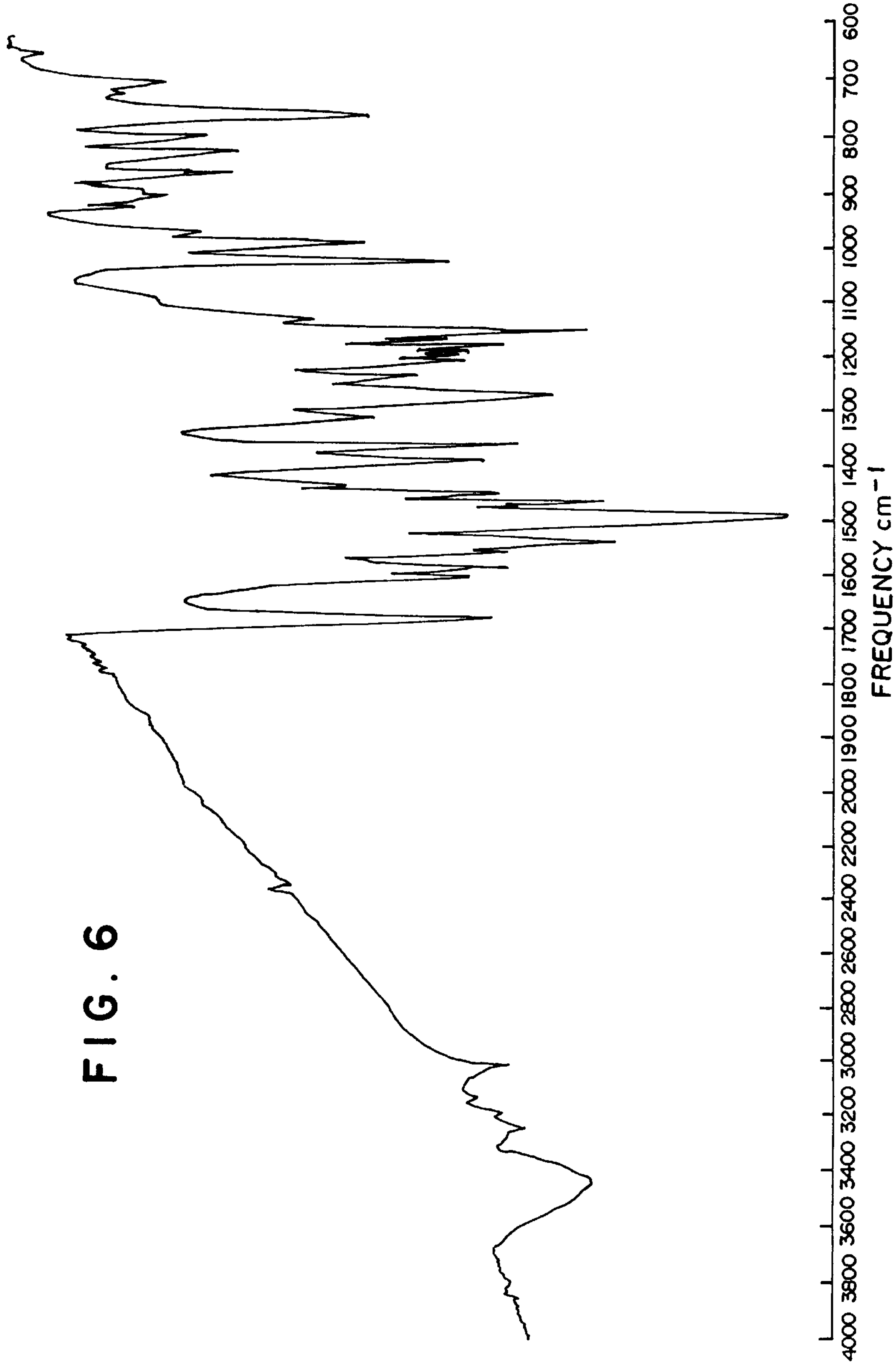

FIG. 6 shows an IR spectrum of the bisazo compound No. 2, taken by use of a KBr tablet.

The IR spectrum data of the bisazo compound No. 2 is also shown in TABLE 15.

EXAMPLE 1-3

Preparation of Bisazo Compound No. 3

0.705 g (2 mmol) of 2-hydroxy-3-phenylcarbamoyl-11H-benzo[a]carbazole (coupler No. 60 in TABLE 2) was dissolved in 100 ml of dimethylformamide (DMF) to prepare a solution. 0.562 g (1 mmol) of 1,4-bis[4-(phenyl-4-diazonium tetrafluoroborate)-1,3-butadienyl]benzene represented by the following formula (IX), that is, the bis (diazonium salt) compound synthesized in Synthesis Example 4, was added to the above-mentioned DMF solution, and thereafter, an aqueous solution prepared by dissolving 0.544 g (4 mmol) of sodium acetate·3 hydrate in 3 ml of water was added dropwise to the reaction mixture over a period of 20 minutes at room temperature.

(IX)

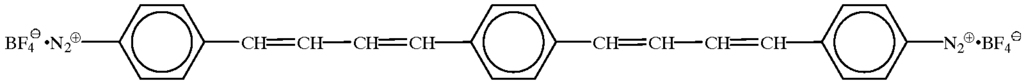

EXAMPLE 1-2

Preparation of Bisazo Compound No. 2

The procedure for preparation of the bisazo compound No. 1 in Example 1-1 was repeated except that the coupler No. 1 employed in Example 1-1 was replaced by the coupler No. 152 in TABLE 6, so that a bisazo compound No. 2 according to the present invention was obtained.

The structural formula of the coupler employed, the yield and the results of the elemental analysis of the bisazo compound No. 2 are shown in TABLE 15.

The above prepared reaction mixture was stirred at room temperature for 2 hours, thereby obtaining a bisazo compound. The thus obtained bisazo compound was filtered off, and successively washed with 100 ml of dimethylformamide three times, and washed with 100 ml of water twice. The compound was then dried with the application of heat thereto under reduced pressure, so that 0.813 g of a bisazo compound No. 3 according to the present invention, represented by the following formula (XI), was obtained in a 74.5% yield.

(XI)

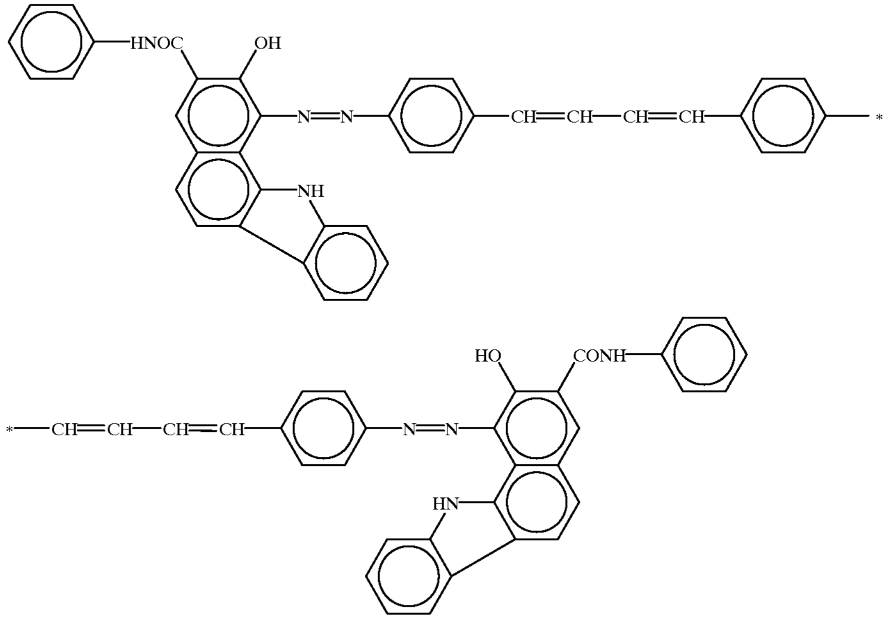

The results of the elemental analysis of the thus obtained bisazo compound No. 3 were as follows:

| | % C | % H | % N |
|---|---|---|---|
| Calculated | 79.25 | 4.62 | 10.27 |
| Found | 79.37 | 4.60 | 9.96 |

Figure 7:
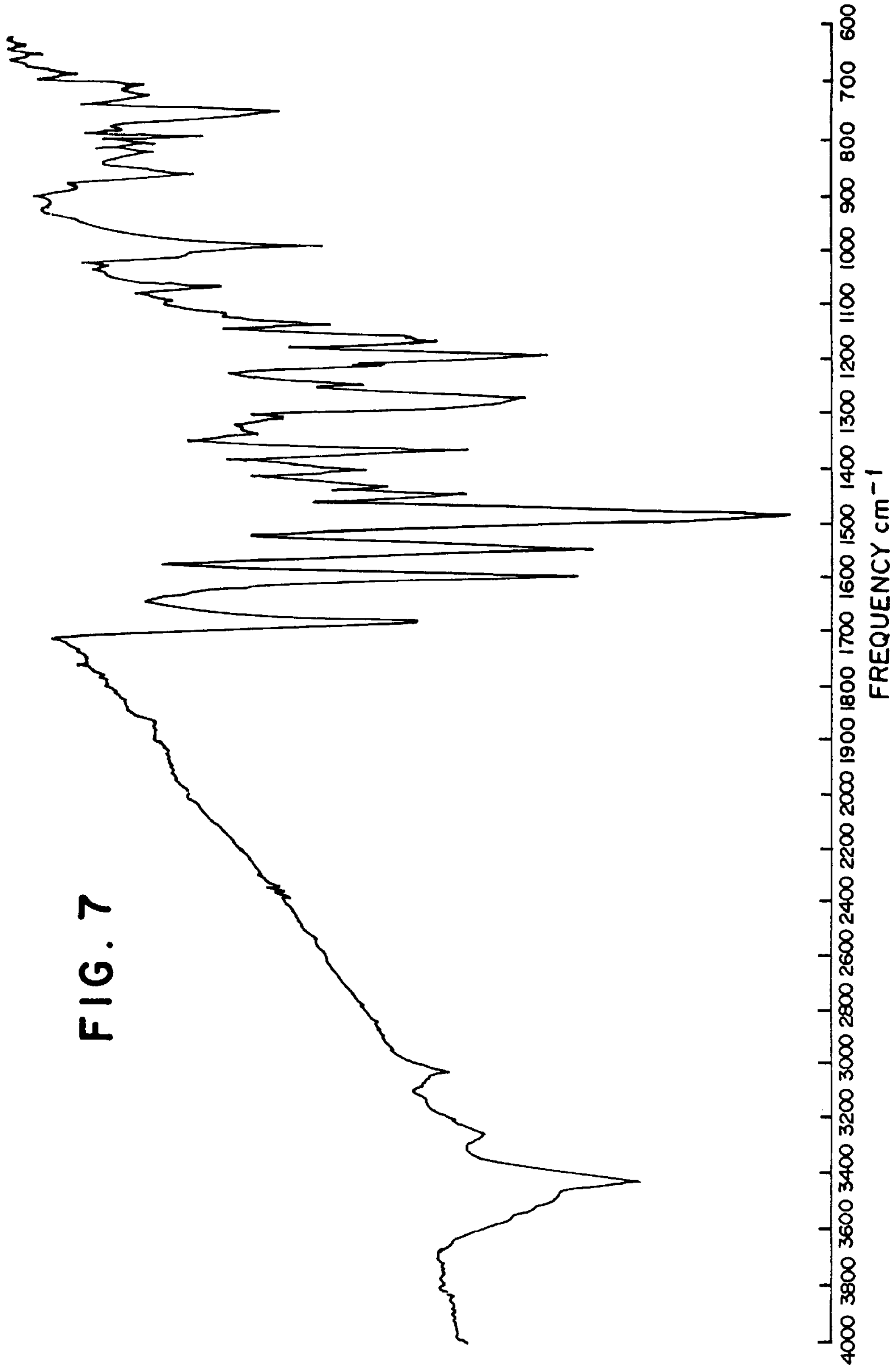

FIG. 7 shows an IR spectrum of the bisazo compound No. 3, taken by use of a KBr tablet.

The IR absorption of the above obtained bisazo compound indicates the appearance of the characteristic absorption peak based on C═O stretching vibration at 1670 $cm^{-1}$, and the characteristic absorption peak based on the C—H out-of-plane deformation vibration of the trans-olefin in the compound at 980 $cm^{-1}$.

EXAMPLE 1-4

Preparation of Bisazo Compound No. 4

The procedure for preparation of the bisazo compound No. 1 in Example 1-1 was repeated except that the coupler No. 1 employed in Example 1-1 was replaced by the coupler No. 201 in TABLE 13, so that a bisazo compound No. 4 according to the present invention was obtained.

The structural formula of the coupler, the yield and the results of the elemental analysis of the bisazo compound No. 4 are shown in TABLE 15.

Figure 8:
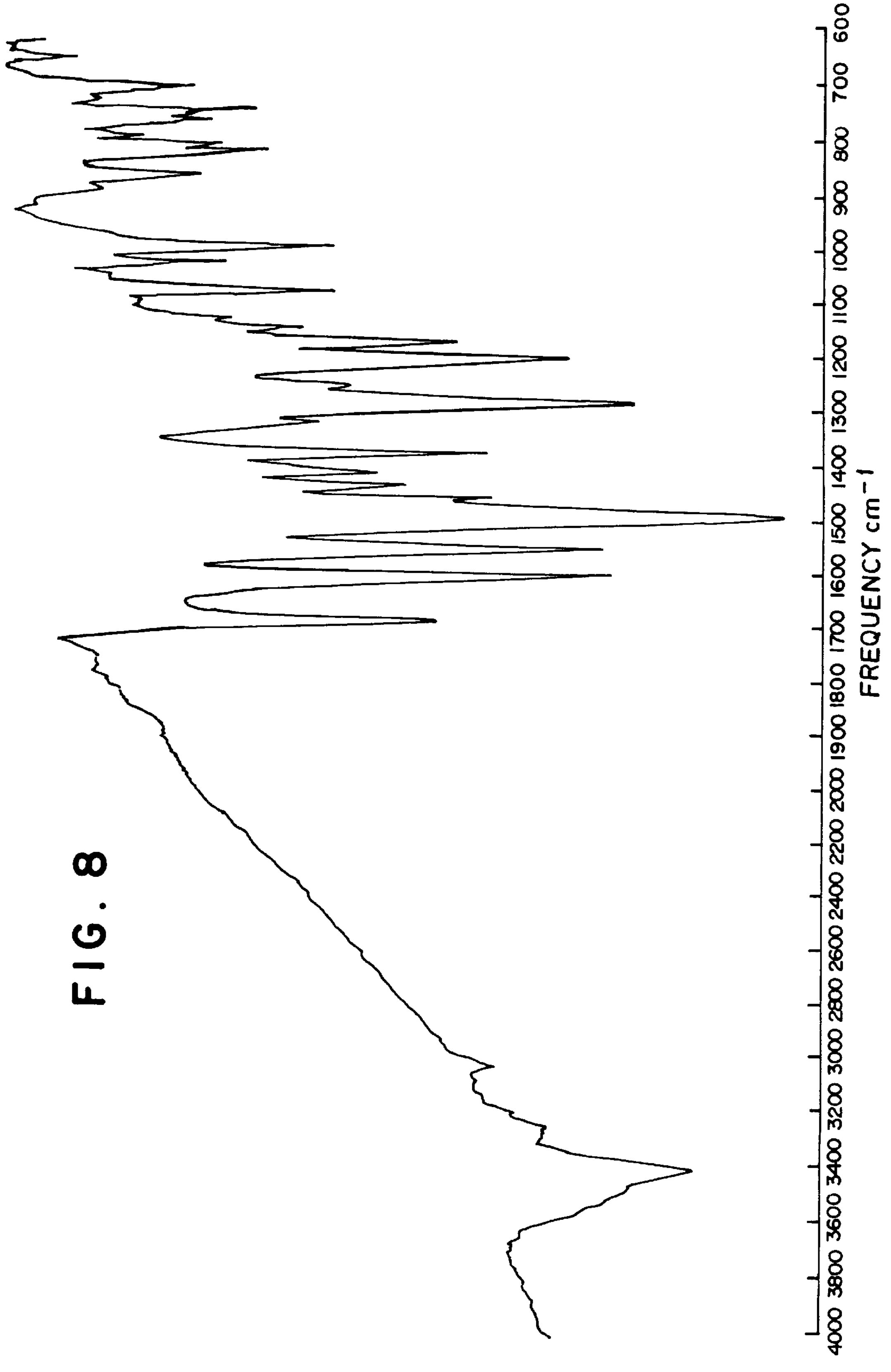

FIG. 8 shows an IR spectrum of the bisazo compound No. 4, taken by use of a KBr tablet. The IR spectrum data of the bisazo compound No. 4 is also shown in TABLE 15.

TABLE 15

| Ex. No. | Cp | Yield (%) | Elemental Analysis (Calculated) Found % C | % H | % N | IR Spectrum (*) |
|---|---|---|---|---|---|---|
| 1-2 | (No. 152) 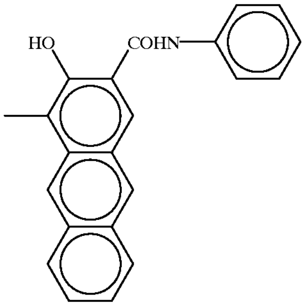 | 68.5 | (80.61) 80.77 | (4.78) 4.60 | (8.29) 8.17 | 1675 980 |

(No. 60)

TABLE 15-continued

| Ex. No. | Cp | Yield (%) | Elemental Analysis (Calculated) Found % C | % H | % N | IR Spectrum (*) |
|---|---|---|---|---|---|---|
| 1-3 | 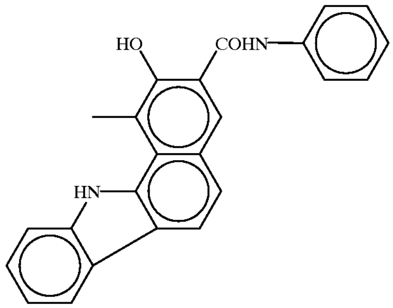 (No. 201) | 74.5 | (79.25) 79.37 | (4.62) 4.60 | (10.27) 9.96 | 1670 980 |
| 1-4 | 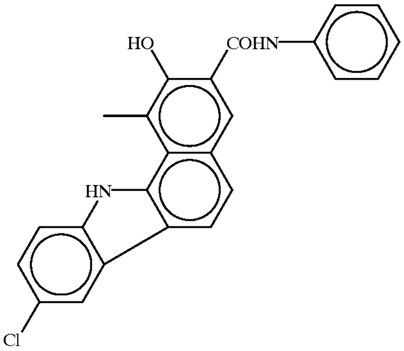 | 70.6 | (74.54) 74.76 | (4.17) 4.13 | (9.66) 9.39 | 1670 980 |

(*) The IR absorption of each bisazo compound indicates the appearance of the characteristic absorption peak based on C═O stretching vibration at the frequency listed above, and the characteristic absorption peak based on the C—H out-of-plane deformation vibration of the transolefin in the compound at the frequency listed below.

EXAMPLES 1-5 TO 1-8

Preparation of Bisazo Compounds No. 5 to No. 8

The procedure for preparation of the bisazo compound No. 1 in Example 1-1 was repeated except that the coupler No. 1 employed in Example 1-1 was replaced by the coupler No. 18, the coupler No. 70, the coupler No. 216 and the coupler No. 247, respectively in Examples 1-5, 1-6, 1-7 and 1-8.

Thus, bisazo compounds No. 5 to No. 8 according to the present invention were obtained.

EXAMPLE 1-9

Preparation of Bisazo Compound No. 9

0.89 g (3 mmol) of 2-hydroxy-3-(2-chlorophenylcarbamoyl)naphthalene (coupler No. 17 in TABLE 1) was dissolved in 120 ml of dimethylformamide (DMF) to prepare a solution. 1.67 g (3 mmol) of 1,4-bis[4-(phenyl-4-diazonium tetrafluoroborate)-1,3-butadienyl] benzene, that is, the bis(diazonium salt) compound synthesized in Synthesis Example 4, was added to the above-mentioned DMF solution at room temperature. The resultant mixture was stirred at room temperature for 10 minutes.

Thereafter, to the above-mentioned reaction mixture, a solution consisting of 1.19 g (3 mmol) of 2-hydroxy-3-[3-nitrophenylcarbamoyl]-11H-benzo[a]carbazole (coupler No. 62 in TABLE 2) and 120 ml of dimethylformamide was added. Subsequently, an aqueous solution prepared by dissolving 1.63 g (12 mmol) of sodium acetate·3 hydrate in 9 ml of water was added dropwise to the above prepared reaction mixture over a period of 20 minutes at room temperature.

The above prepared reaction mixture was stirred at room temperature for 2 hours, and the precipitating product was filtered off, and successively washed with 240 ml of dimethylformamide of 80° C. three times, and washed with 240 ml of water twice. The compound was then dried at 120° C. under reduced pressure, so that 2.26 g of a bisazo compound No. 9 according to the present invention, represented by the following formula (XII), was obtained in a 69.9% yield.

(XII)

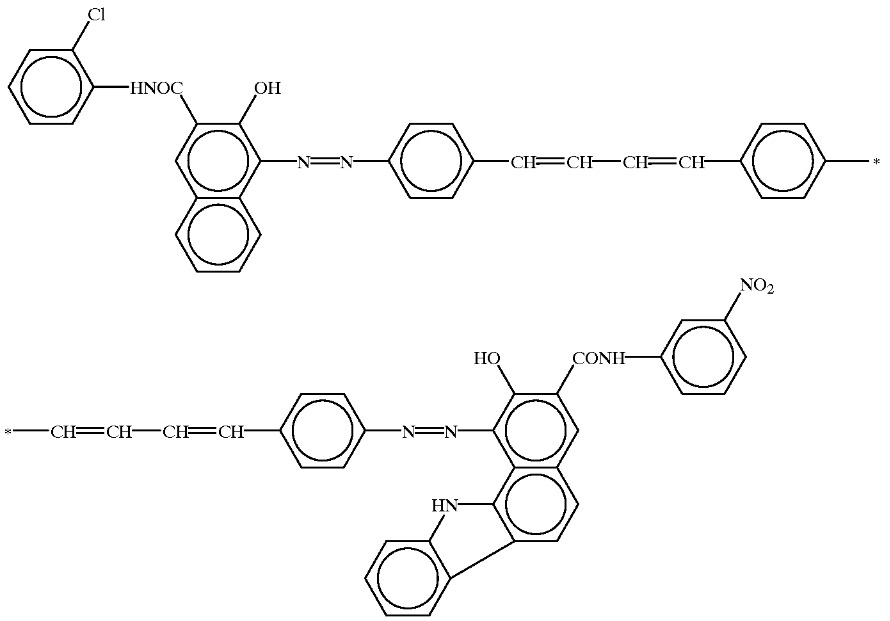

EXAMPLES 1-10 TO 1-12

Preparation of Bisazo Compounds No. 10 to No. 12

The procedure for preparation of the bisazo compound No. 9 in Example 1-9 was repeated except that the combination of the couplers No. 17 and No. 62 employed in Example 1-9 was replaced by the combination of the couplers No. 200 and No. 239, the combination of the couplers No. 205 and No. 136, and the combination of the couplers No. 214 and No. 248, respectively in Examples 1-10, 1-11 and 1-12.

Thus, bisazo compounds No. 10 to No. 12 according to the present invention were obtained.

EXAMPLE 2-1

Fabrication of Photoconductor No. 1

(Formation of charge generation layer)

7.5 parts by weight of the bisazo compound No. 1 (prepared in Example 1-1) and 500 parts by weight of a 0.5% tetrahydrofuran solution containing 2.5 parts by weight of a commercially available polyester resin (Trademark "Vylon 200" made by Toyobo Company, Ltd.) were dispersed and ground in a ball mill, so that a coating liquid for a charge generation layer was prepared.

The thus prepared coating liquid was coated on the aluminum-deposited surface of an aluminum-deposited polyester film by a doctor blade, and dried at room temperature, so that a charge generation layer with a thickness of about 1 μm was formed on the aluminum-deposited polyester film.

(Formation of charge transport layer)

One part by weight of the commercially available polycarbonate resin (Trademark "Panlite K-1300" made by Teijin Limited.) was dissolved in 8 parts by weight of tetrahydrofuran so as to prepare a resin solution. One part by weight of α-phenyl-4'-diphenylaminostilbene serving as a charge transport material was dissolved in the above-mentioned resin solution, so that a coating liquid for a charge transport layer was prepared.

The thus prepared coating liquid was coated on the charge generation layer by a doctor blade, and thereafter dried at 80° C. for 2 minutes and then 120° C. for 5 minutes, so that a charge transport layer with a thickness of about 20 μm was provided on the charge generation layer.

Thus, an electrophotographic photoconductor No. 1 according to the present invention was fabricated.

EXAMPLES 2-2 to 2-8

The procedure for fabrication of the electrophotographic photoconductor No. 1 in Example 2-1 was repeated except that the bisazo compound No. 1 (prepared in Example 1-1) for use in the charge generation layer coating liquid in Example 2-1 was replaced by the respective bisazo compounds No. 2 to No. 8 (prepared in Examples 1-2 to 1-8).

Thus, electrophotographic photoconductors No. 2 to No. 8 according to the present invention were fabricated.

Each of the electrophotographic photoconductors No. 1 to No. 8 according to the present invention fabricated in Examples 2-1 to 2-8 was negatively charged in the dark under application of −6 kV of corona charge for 20 seconds using a commercially available electrostatic copying sheet testing apparatus "Paper Analyzer Model EPA8100™" made by Kawaguchi Electro Works Co., Ltd. Then, each photoconductor was allowed to stand in the dark for 20 seconds without applying any charge thereto, and the surface potential Vo (V) of each photoconductor was measured. Each photoconductor was then illuminated by a tungsten lamp in such a manner that the illuminance on the illuminated surface of the photoconductor was 5.3 lux. The exposure $E_{1/2}$ (lux·sec) required to reduce the initial surface potential Vo (V) to ½ the initial surface potential Vo (V) was calculated so as to obtain the sensitivity in the visible light range.

The results are shown in TABLE 16.

TABLE 16

| Example No. | Photo-conductor No. | Bisazo Compound No. | Coupler No. | Vo (V) | $E_{1/2}$ (lux · sec) |
|---|---|---|---|---|---|
| 2-1 | 1 | 1 | 1 | −1079 | 1.99 |
| 2-2 | 2 | 2 | 152 | −787 | 1.20 |
| 2-3 | 3 | 3 | 60 | −914 | 1.29 |
| 2-4 | 4 | 4 | 201 | −778 | 1.56 |
| 2-5 | 5 | 5 | 18 | −1120 | 1.02 |
| 2-6 | 6 | 6 | 70 | −1011 | 1.01 |
| 2-7 | 7 | 7 | 216 | −1047 | 0.86 |
| 2-8 | 8 | 8 | 247 | −921 | 1.55 |

EXAMPLE 2-9

The procedure for fabrication of the electrophotographic photoconductor No. 1 in Example 2-1 was repeated except that α-phenyl-4'-diphenylaminostilbene serving as the charge transport material for use in the charge transport layer coating liquid in Example 2-1 was replaced by α-phenyl-4'-bis(4-methylphenyl)aminostilbene represented by the following formula (XIII).

(XIII)

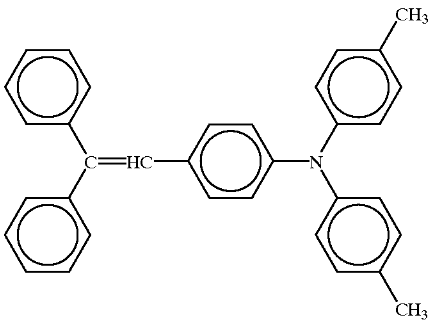

Thus, an electrophotographic photoconductor No. 9 according to the present invention was fabricated.

EXAMPLE 2-10

The procedure for fabrication of the electrophotographic photoconductor No. 2 in Example 2-2 was repeated except that α-phenyl-4'-diphenylaminostilbene serving as the charge transport material for use in the charge transport layer coating liquid in Example 2-2 was replaced by α-phenyl-4'-bis(4-methylphenyl)aminostilbene of formula (XIII).

Thus, an electrophotographic photoconductor No. 10 according to the present invention was fabricated.

EXAMPLE 2-11

The procedure for fabrication of the electrophotographic photoconductor No. 3 in Example 2-3 was repeated except that α-phenyl-4'-diphenylaminostilbene serving as the charge transport material for use in the charge transport layer coating liquid in Example 2-3 was replaced by α-phenyl-4'-bis(4-methylphenyl)aminostilbene of formula (XIII).

Thus, an electrophotographic photoconductor No. 11 according to the present invention was fabricated.

EXAMPLE 2-12

The procedure for fabrication of the electrophotographic photoconductor No. 4 in Example 2-4 was repeated except that α-phenyl-4'-diphenylaminostilbene serving as the charge transport material for use in the charge transport layer coating liquid in Example 2-4 was replaced by α-phenyl-4'-bis(4-methylphenyl)aminostilbene of formula (XIII).

Thus, an electrophotographic photoconductor No. 12 according to the present invention was fabricated.

EXAMPLE 2-13

The procedure for fabrication of the electrophotographic photoconductor No. 5 in Example 2-5 was repeated except that α-phenyl-4'-diphenylaminostilbene serving as the charge transport material for use in the charge transport layer coating liquid in Example 2-5 was replaced by α-phenyl-4'-bis(4-methylphenyl)aminostilbene of formula (XIII).

Thus, an electrophotographic photoconductor No. 13 according to the present invention was fabricated.

EXAMPLE 2-14

The procedure for fabrication of the electrophotographic photoconductor No. 6 in Example 2-6 was repeated except that α-phenyl-4'-diphenylaminostilbene serving as the charge transport material for use in the charge transport layer coating liquid in Example 2-6 was replaced by α-phenyl-4'-bis(4-methylphenyl)aminostilbene of formula (XIII).

Thus, an electrophotographic photoconductor No. 14 according to the present invention was fabricated.

EXAMPLE 2-15

The procedure for fabrication of the electrophotographic photoconductor No. 7 in Example 2-7 was repeated except that α-phenyl-4'-diphenylaminostilbene serving as the charge transport material for use in the charge transport layer coating liquid in Example 2-7 was replaced by α-phenyl-4'-bis(4-methylphenyl)aminostilbene of formula (XIII).

Thus, an electrophotographic photoconductor No. 15 according to the present invention was fabricated.

EXAMPLE 2-16

The procedure for fabrication of the electrophotographic photoconductor No. 8 in Example 2-8 was repeated except that α-phenyl-4'-diphenylaminostilbene serving as the charge transport material for use in the charge transport layer coating liquid in Example 2-8 was replaced by α-phenyl-4'-bis(4-methylphenyl)aminostilbene of formula (XIII).

Thus, an electrophotographic photoconductor No. 16 according to the present invention was fabricated.

Each of the electrophotographic photoconductors No. 9 to No. 16 according to the present invention fabricated in Examples 2-9 to 2-16 was negatively charged in the dark under application of −6 kV of corona charge for 20 seconds using a commercially available electrostatic copying sheet testing apparatus "Paper Analyzer Model EPA8100™" made by Kawaguchi Electro Works Co., Ltd. Then, each photoconductor was allowed to stand in the dark for 20 seconds without applying any charge thereto, and the surface potential Vo (V) of each photoconductor was measured. Each photoconductor was then illuminated by a tungsten lamp in such a manner that the illuminance on the illuminated surface of the photoconductor was 5.3 lux. The exposure $E_{1/2}$ (lux·sec) required to reduce the initial surface potential Vo (V) to ½ the initial surface potential Vo (V) was calculated so as to obtain the sensitivity in the visible light range.

The results are shown in TABLE 17.

TABLE 17

| Example No. | Photo-conductor No. | Bisazo Compound No. | Coupler No. | Vo (V) | $E_{1/2}$ (lux · sec) |
|---|---|---|---|---|---|
| 2-9 | 9 | 1 | 1 | −865 | 1.29 |
| 2-10 | 10 | 2 | 152 | −673 | 0.98 |
| 2-11 | 11 | 3 | 60 | −752 | 0.84 |
| 2-12 | 12 | 4 | 201 | −635 | 0.76 |
| 2-13 | 13 | 5 | 18 | −1056 | 0.74 |
| 2-14 | 14 | 6 | 70 | −1022 | 0.69 |
| 2-15 | 15 | 7 | 216 | −1116 | 0.75 |
| 2-16 | 16 | 8 | 247 | −822 | 1.03 |

EXAMPLES 2-17 TO 2-20

The procedure for fabrication of the electrophotographic photoconductor No. 9 in Example 2-9 was repeated except that the bisazo compound No. 1 (prepared in Example 1-1) for use in the charge generation layer coating liquid in Example 2-9 was replaced by the bisazo compounds No. 9 to No. 12, respectively in Examples 2-17 to 2-20.

Thus, electrophotographic photoconductors No. 17 to No. 20 according to the present invention were fabricated.

Each of the electrophotographic photoconductors No. 17 to No. 20 according to the present invention fabricated in Examples 2-17 to 2-20 was negatively charged in the dark under application of −6 kV of corona charge for 20 seconds using a commercially available electrostatic copying sheet testing apparatus "Paper Analyzer Model EPA8100™" made by Kawaguchi Electro Works Co., Ltd. Then, each photoconductor was allowed to stand in the dark for 20 seconds without applying any charge thereto, and the surface potential Vo (V) of each photoconductor was measured. Each photoconductor was then illuminated by a tungsten lamp in such a manner that the illuminance on the illuminated surface of the photoconductor was 5.3 lux. The exposure $E_{1/2}$ (lux·sec) required to reduce the initial surface potential Vo (V) to ½ the initial surface potential Vo (V) was calculated so as to obtain the sensitivity in the visible light range.

The results are shown in TABLE 18.

TABLE 18

| Example No. | Photo-conductor No. | Bisazo Compound No. | Coupler No. | Vo (V) | $E_{1/2}$ (lux · sec) |
|---|---|---|---|---|---|
| 2-17 | 17 | 9 | 17 & 62 | −1054 | 1.24 |
| 2-18 | 18 | 10 | 200 & 239 | −979 | 0.68 |
| 2-19 | 19 | 11 | 205 & 136 | −888 | 0.43 |
| 2-20 | 20 | 12 | 214 & 248 | −841 | 0.38 |

Furthermore, using the photoconductors Nos. 3, 11, 14, 20 and 15, the sensitivity of the photoconductor with respect to the semiconductor laser beam was examined in the following manner. Each photoconductor was negatively charged in the dark by corona charge using a commercially available electrostatic copying sheet testing apparatus "Paper Analyzer Model EPA8100™" made by Kawaguchi Electro Works Co., Ltd., and then allowed to stand in the dark without applying any change thereto. When the surface potential of the photoconductor reached −800 V, the photoconductor was illuminated by a 780 nm-monochromatic light pf 1 $\mu W/cm^2$. The period of time (s) required to reduce the surface potential (−800 V) to 2/1 the surface potential (−400 V) and the exposure ($\mu W \cdot s \cdot cm^{-2}$) were obtained. Thus, a photo-induced discharge speed ($C \cdot cm^2/\mu J$) was calculated.

The results are shown in TABLE 19.

TABLE 19

| Photoconductor No. | S ($V \cdot cm^2/\mu J$) |
|---|---|
| 3 | 620 |
| 11 | 930 |
| 14 | 1250 |
| 20 | 1630 |
| 15 | 1120 |

As can be seen from the above-mentioned results, the photoconductors employing the bisazo compounds according to the present invention can show remarkably high sensitivity not only in the visible region, but also in the near infrared region.

EXAMPLE 2-21

Fabrication of Layered Photoconductor (Formation of charge generation layer)

A mixture of one part by weight of the bisazo compound No. 3 obtained in Example 1-3, 50 parts by weight of a butyl acetate solution containing 2 wt. % of a commercially available polyvinyl butyral resin (Trademark "S-Lec BMS", made by Sekisui Chemical Co., Ltd.) and 49 parts by weight of n-butyl acetate was dispersed for 2 hours in a sand mill using 2-mm diameter glass beads, so that a coating liquid for a charge generation layer was prepared.

The thus prepared charge generation layer coating liquid was coated on the aluminum-deposited surface of an aluminum-deposited polyester film serving as an electroconductive support, and dried at 80° C. for 5 minutes. Thus, a charge generation layer with a thickness of about 0.5 $\mu$m was provided on the electroconductive support.

(Formation-of charge transport layer)

64 parts by weight of an electron transport material represented by the following formula (XIV) and 96 parts by weight of a commercially available polycarbonate resin (Trademark "IUPILON Z200" made by Mitsubishi Gas Chemical Company, Inc.) were dissolved in 640 parts by weight of tetrahydrofuran, so that a coating liquid for a charge transport layer was prepared.

(XIV)

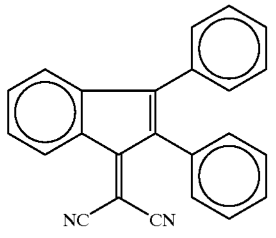

The thus prepared charge transport layer coating liquid was coated on the above prepared charge generation layer using a doctor blade, and dried at 110° C. for 10 minutes, so that a charge transport layer with a thickness of about 25 μm was provided on the charge generation layer.

Thus, an electrophotographic photoconductor No. 21 according to the present invention was fabricated.

EXAMPLE 2-22

The procedure for fabrication of the electrophotographic photoconductor No. 21 in Example 2-21 was repeated except that the electron transport material of formula (XIV) for use in the charge transport layer coating liquid in Example 2-21 was replaced by an electron transport material of the following formula (XV):

(XV)

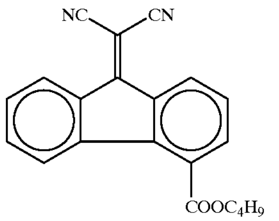

Thus, an electrophotographic photoconductor No. 22 according to the present invention was fabricated.

EXAMPLE 2-23

The procedure for fabrication of the electrophotographic photoconductor No. 21 in Example 2-21 was repeated except that the electron transport material of formula (XIV) for use in the charge transport layer coating liquid in Example 2-21 was replaced by an electron transport material of the following formula (XVI):

(XVI)

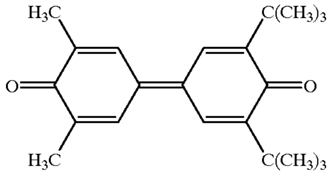

Thus, an electrophotographic photoconductor No. 23 according to the present invention was fabricated.

EXAMPLE 2-24

Fabrication of Single-layered Photoconductor

A mixture of one part by weight of the bisazo compound No. 12 obtained in Example 1-12 and 158 parts by weight of methyl ethyl ketone was dispersed in a ball mill using 5-mm diameter alumina balls for 24 hours. To the above prepared mixture, 12 parts by weight of α-phenyl-4'-diphenylaminostilbene serving as the charge transport material and 18 parts by weight of a commercially available polycarbonate resin (Trademark "IUPILON Z200" made by Mitsubishi Gas Chemical Company, Inc.) were added, and the resultant mixture was dispersed, so that a coating liquid for a photoconductive layer was prepared. The thus prepared coating liquid was coated on the aluminum-deposited surface of an aluminum-deposited polyester film using a doctor blade, and dried at 100° C. for 30 minutes, so that a photoconductive layer with a thickness of about 15 μm was provided on the electroconductive support.

Thus, an electrophotographic photoconductor No. 24 according to the present invention was fabricated.

Each of the electrophotographic photoconductors No. 21 to No. 24 according to the present invention fabricated in Examples 2-21 to 2-24 was positively charged in the dark under application of +6 kV of corona charge for 20 seconds using a commercially available electrostatic copying sheet testing apparatus "Paper Analyzer Model EPA8100™" made by Kawaguchi Electro Works Co., Ltd. Then, each photoconductor was allowed to stand in the dark for 20 seconds without applying any charge thereto, and the surface potential Vo (V) of each photoconductor was measured. Each photoconductor was then illuminated by a tungsten lamp in such a manner that the illuminance on the illuminated surface of the photoconductor was 5.3 lux. The exposure $E_{1/2}$ (lux·sec) required to reduce the initial surface potential Vo (V) to ½ the initial surface potential Vo (V) was calculated so as to obtain the sensitivity in the visible light range.

The results are shown in TABLE 20.

TABLE 20

| Example No. | Photo-conductor No. | Bisazo Compound No. | Vo (V) | $E_{1/2}$ (lux · sec) |
|---|---|---|---|---|
| 2-21 | 21 | 3 | +1021 | 2.56 |
| 2-22 | 22 | 3 | +954 | 2.68 |
| 2-23 | 23 | 3 | +1035 | 2.87 |
| 2-24 | 24 | 12 | +681 | 1.95 |

COMPARATIVE EXAMPLE 2-1

The procedure for fabrication of the electrophotographic photoconductor No. 14 in Example 2-14 was repeated except that the bisazo compound No. 6 (prepared in Example 1-6) for use in the charge generation layer coating liquid in Example 2-14 was replaced by a comparative bisazo compound represented by the following formula (XVII):

(XVII)

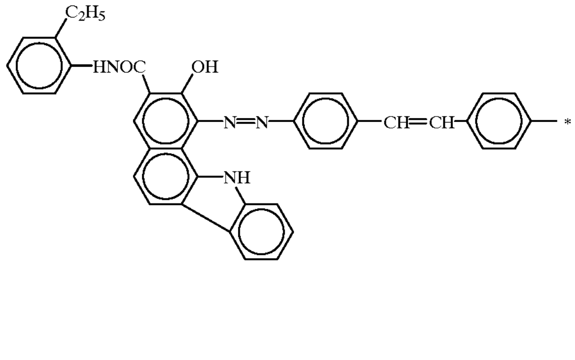

-continued

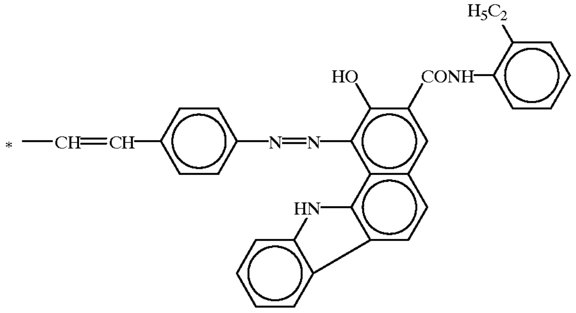

Thus, a comparative electrophotographic photoconductor No. 1 was fabricated.

Using the comparative photoconductor No. 1, the sensitivity of the photoconductor with respect to the semiconductor laser beam was examined in the following manner. The photoconductor was negatively charged in the dark by corona charge using a commercially available electrostatic copying sheet testing apparatus "Paper Analyzer Model EPA8100™" made by Kawaguchi Electro Works Co., Ltd., and then allowed to stand in the dark without applying any charge thereto. When the surface potential of the photoconductor reached −800 V, the photoconductor was illuminated by a 780 nm-monochromatic light of 1 $\mu W/cm^2$. The period of time (s) required to reduce the surface potential (−800 V) to 2/1 the surface potential (−400 V) and the exposure ($\alpha W \cdot s \cdot cm^2$) were obtained. As a result, the photo-induced discharge speed of the comparative photoconductor No. 1 was 23 $V \cdot cm^2/\mu J$.

As compared with the comparative electrophotographic photoconductor No. 1, the photoconductor No. 14 employing the bisazo compound No. 6 according to the present invention can show remarkably high sensitivity with respect to the near infrared light as show in TABLE 19, so that the photoconductor of the present invention is considered to be suitable for the digital copying machine and laser printer.

Japanese Patent Application No. 10-095969 filed Apr. 8, 1998, Japanese Patent Application No. 10-139974 filed May 21, 1998, Japanese Patent Application No. 10-253905 filed Sep. 8, 1998 and Japanese Patent Application No. 11-030873 filed Feb. 9, 1999 are hereby incorporated by reference.

What is claimed is:

1. 1,4-bis[4-(4-nitrophenyl)-1,3-butadienyl]benzene represented by formula (V):

(V)

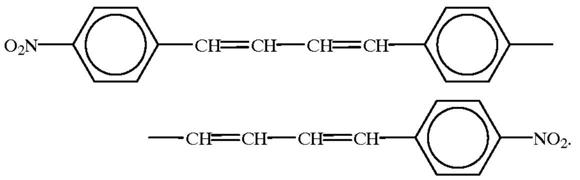

2. A method of producing 1,4-bis[4-(4-nitrophenyl)-1,3-butadienyl]benzene of formula (V) comprising the step of allowing a bis(phosphonium salt) compound of formula (VII) to react with 4-nitrocinnamaldehyde:

(V)

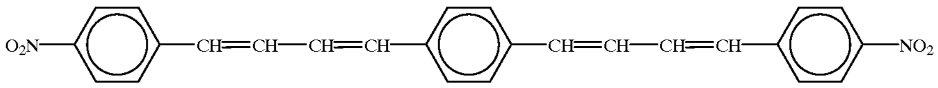

(VII)

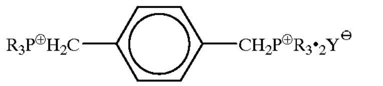

wherein R is phenyl group or an alkyl group; and $Y^{\ominus}$ is a halogen ion.

3. A method of producing 1,4-bis[4-(4-nitrophenyl)-1,3-butadienyl]benzene of formula (V) comprising the step of allowing a phosphonate of formula (VIII) to react with terephthalaldehyde:

(V)

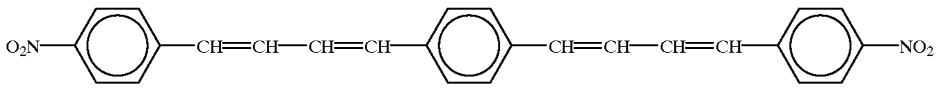

(VIII)

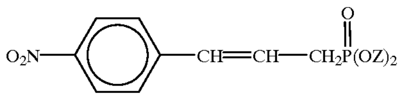

wherein Z is a lower alkyl group.

* * * * *

UNITED STATES PATENT AND TRADEMARK OFFICE

CERTIFICATE OF CORRECTION

PATENT NO. : 6,333,439 B1
DATED : December 25, 2001
INVENTOR(S) : Tomoyuki Shimada It is certified that error appears in the above-identified patent and that said Letters Patent is hereby corrected as shown below:

Column 3,
Line 39, "The-second" should read -- The second --.

Columns 13-14,
Delete Table 1 and replace with --

TABLE 1

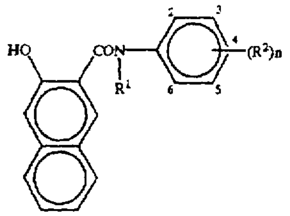

| Coupler No. | $R^1$ | $(R^2)_n$ | Melting Point (° C.) |
|---|---|---|---|
| 1 | H | H | 243–244 |
| 2 | H | 2-$NO_2$ | 194–196 |
| 3 | H | 3-$NO_2$ | 246–247 |
| 4 | H | 4-$NO_2$ | 266–267.5 |
| 5 | H | 2-$CF_3$ | 178–179 |
| 6 | H | 3-$CF_3$ | 237.5–238.5 |
| 7 | H | 4-$CF_3$ | 279–281 |
| 8 | H | 2-CN | 221–222.5 |
| 9 | H | 3-CN | 256.5–258.5 |
| 10 | H | 4-CN | 274.5–277 |
| 11 | H | 2-I | 199–199.5 |
| 12 | H | 3-I | 258.5–259.5 |
| 13 | H | 4-I | 261.5–262 |
| 14 | H | 2-Br | 217–218 |
| 15 | H | 3-Br | 254–255 |
| 16 | H | 4-Br | 265–268 |
| 17 | H | 2-Cl | 228–230 |
| 18 | H | 3-Cl | 256.5–257 |
| 19 | H | 4-Cl | 264–266 |
| 20 | H | 2-F | 223.0–224.0 |
| 21 | H | 3-F | 250.0–251.0 |
| 22 | H | 4-F | 265.0–267.0 |
| 23 | H | 2-$CH_3$ | 195.5–198.0 |
| 24 | H | 3-$CH_3$ | 214.5–216.5 |
| 25 | H | 4-$CH_3$ | 227.0–229.0 |
| 26 | H | 2-$C_2H_5$ | 168.5–169.5 |
| 27 | H | 4-$C_2H_5$ | 203.0–204.5 |
| 28 | H | 2-$OCH_3$ | 167–168 |

CERTIFICATE OF CORRECTION

PATENT NO. : 6,333,439 B1
DATED : December 25, 2001
INVENTOR(S) : Tomoyuki Shimada It is certified that error appears in the above-identified patent and that said Letters Patent is hereby corrected as shown below:

| | | | |
|---|---|---|---|
| 29 | H | 3-$OCH_3$ | 195.5–198.0 |
| 30 | H | 4-$OCH_3$ | 229–230 |
| 31 | H | 2-$OC_2H_5$ | 157–158 |
| 32 | H | 3-$OC_2H_5$ | 188.5–189.0 |
| 33 | H | 4-$OC_2H_5$ | 225.0–225.5 |
| 34 | H | 4-$N(CH_3)_2$ | 232.0–233.5 |
| 35 | $-CH_3$ | H | 189.5–190.5 |
| 36 | 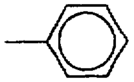 | H | 182.0–183.0 |
| 37 | H | 2-$OCH_3$, 5-$OCH_3$ | 186.0–188.0 |
| 38 | H | 2-$OC_2H_5$, 5-$OC_2H_5$ | 173.0–173.5 |
| 39 | H | 2-$CH_3$, 5-$CH_3$ | 207.0–208.5 |
| 40 | H | 2-Cl, 5-Cl | 253.5–254.5 |
| 41 | H | 2-$CH_3$, 5-Cl | 245–247 |
| 42 | H | 2-$OCH_3$, 4-$OCH_3$ | 151.0–152.0 |
| 43 | H | 2-$CH_3$, 4-$CH_3$ | 226–228 |
| 44 | H | 2-$CH_3$, 4-Cl | 244–245 |
| 45 | H | 2-$NO_2$, 4-$OCH_3$ | 179.5–181.0 |
| 46 | H | 3-$OCH_3$, 5-$OCH_3$ | 180.5–182.0 |
| 47 | H | 2-$OCH_3$, 5-Cl | 219.0–220.0 |
| 48 | H | 2-$OCH_3$, 5-$OCH_3$, 4-Cl | 193.5–195.5 |
| 49 | H | 2-$OCH_3$, 4-$OCH_3$, 5-Cl | 193–194 |
| 50 | H | 3-Cl, 4-Cl | 272.5–273.5 |
| 51 | H | 2-Cl, 4-Cl, 5- | 257.5–258.5 |
| 52 | H | 2-$CH_3$, 3-Cl | 227.5–228.5 |
| 53 | H | 3-Cl, 4-$CH_3$ | 259.5–260.5 |
| 54 | H | 2-F, 4-F | 246.0–246.5 |
| 55 | H | 2-F, 5-F | 259.0–260.0 |

TABLE 1-continued

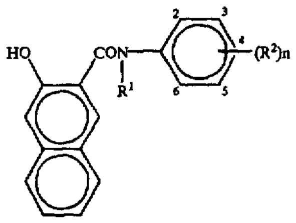

| Coupler No. | $R^1$ | $(R^2)_n$ | Melting Point (° C.) |
|---|---|---|---|
| 56 | H | 2-Cl, 4-$NO_2$ | 283.0–284.0 |
| 57 | H | 2-$NO_2$, 4-Cl | 226.5–227.5 |
| 58 | H | 2-Cl, 3-Cl, 4-Cl, 5-Cl | 280.0–281.5 |
| 59 | H | 4-OH | 268 |

UNITED STATES PATENT AND TRADEMARK OFFICE

CERTIFICATE OF CORRECTION

PATENT NO. : 6,333,439 B1
DATED : December 25, 2001
INVENTOR(S) : Tomoyuki Shimada It is certified that error appears in the above-identified patent and that said Letters Patent is hereby corrected as shown below:

Column 35,
Line 15, "of by formula (I)" should read -- of formula (I) --.

Column 39,
Line 43, "No. 51-109831" should read -- No. 51-10983 --.

Column 43,
Line 10, "or s substituted" should read -- or a substituted --.

Column 65,
Line 64, "eloctrostatic" should read -- electrostatic --.
Line 67, "change" should read -- charge --.

Column 66,
Line 3, "pf" should read -- of --.
Line 6, "(C·cm $^2/\mu J$)"" should read -- (V·cm $^2/\mu J$) --.

Column 69,
Line 46, "($\alpha$W·s·cm$^2$)" should read -- "($\mu$W·s·cm$^2$) --.

Column 70,
Line 2, "show" should read -- shown --.
Line 35,

" 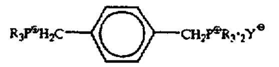 "

should read

-- 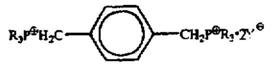 --.

Signed and Sealed this

Fourteenth Day of May, 2002

*Attest:*

JAMES E. ROGAN

*Attesting Officer* *Director of the United States Patent and Trademark Office*